United States Patent
Chui et al.

(10) Patent No.: US 12,070,349 B2
(45) Date of Patent: Aug. 27, 2024

(54) SYSTEM AND METHOD FOR TARGETED OBJECT ENHANCEMENT TO GENERATE SYNTHETIC BREAST TISSUE IMAGES

(71) Applicant: Hologic, Inc., Marlborough, MA (US)

(72) Inventors: Haili Chui, Fremont, CA (US); Liyang Wei, San Jose, CA (US); Jun Ge, Cupertino, CA (US); Nikolaos Gkanatsios, Danbury, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 17/847,720

(22) Filed: Jun. 23, 2022

(65) Prior Publication Data

US 2023/0082494 A1     Mar. 16, 2023

Related U.S. Application Data

(63) Continuation of application No. 16/497,767, filed as application No. PCT/US2018/024913 on Mar. 28, 2018, now Pat. No. 11,445,993.

(Continued)

(51) Int. Cl.
*G06K 9/00*     (2022.01)
*A61B 6/00*     (2006.01)
(Continued)

(52) U.S. Cl.
CPC ............ *A61B 6/5217* (2013.01); *A61B 6/463* (2013.01); *A61B 6/469* (2013.01); *A61B 6/502* (2013.01);
(Continued)

(58) Field of Classification Search
CPC .......... B41M 5/00; G06T 7/0012; G06K 9/00; G03G 13/054
(Continued)

(56) References Cited

U.S. PATENT DOCUMENTS 3,502,878 A     3/1970   Stewart
3,863,073 A     1/1975   Wagner
(Continued)

FOREIGN PATENT DOCUMENTS

AU     2014339982     4/2015
CN     1846622     10/2006
(Continued)

OTHER PUBLICATIONS

"Filtered Back Projection", (NYGREN), published May 8, 2007, URL: http://web.archive.org/web/19991010131715/http://www.owlnet.rice.edu/~elec539/Projects97/cult/node2.html, 2 pgs.
(Continued)

*Primary Examiner* — Seyed H Azarian
(74) *Attorney, Agent, or Firm* — Merchant & Gould P.C.

(57) ABSTRACT

A method for processing breast tissue image data includes obtaining image data of a patient's breast tissue, processing the image data to generate a set of image slices, the image slices collectively depicting the patient's breast tissue; feeding image slices of the set through each of a plurality of object-recognizing modules, each of the object-recognizing modules being configured to recognize a respective type of object that may be present in the image slices; combining objects recognized by the respective object-recognizing modules to generate a synthesized image of the patient's breast tissue; and displaying the synthesized image.

14 Claims, 11 Drawing Sheets

Related U.S. Application Data

(60) Provisional application No. 62/479,036, filed on Mar. 30, 2017.

(51) Int. Cl.
| | |
|---|---|
| *A61B 6/46* | (2024.01) |
| *A61B 6/50* | (2024.01) |
| *G03G 13/054* | (2006.01) |
| *G06T 5/00* | (2006.01) |
| *G06T 5/50* | (2006.01) |
| *G06T 7/00* | (2017.01) |
| *A61B 6/02* | (2006.01) |

(52) U.S. Cl.
CPC .......... *A61B 6/5205* (2013.01); *A61B 6/5235* (2013.01); *G06T 5/00* (2013.01); *G06T 5/50* (2013.01); *G06T 7/0012* (2013.01); *A61B 6/025* (2013.01); *G06T 2200/24* (2013.01); *G06T 2207/10112* (2013.01); *G06T 2207/20221* (2013.01); *G06T 2207/30068* (2013.01)

(58) Field of Classification Search
USPC ....... 382/100, 103, 128–134, 154, 162, 172, 382/173, 178, 181, 189, 219, 224, 254, 382/255, 276, 285, 305, 321; 715/771; 378/4, 21, 28
See application file for complete search history.

(56) References Cited

U.S. PATENT DOCUMENTS

| | | |
|---|---|---|
| 3,971,950 A | 7/1976 | Evans et al. |
| 4,160,906 A | 7/1979 | Daniels |
| 4,310,766 A | 1/1982 | Finkenzeller et al. |
| 4,496,557 A | 1/1985 | Malen et al. |
| 4,559,557 A | 12/1985 | Keyes |
| 4,559,641 A | 12/1985 | Caugant et al. |
| 4,706,269 A | 11/1987 | Reina et al. |
| 4,727,565 A | 2/1988 | Ericson |
| 4,744,099 A | 5/1988 | Huettenrauch |
| 4,773,086 A | 9/1988 | Fujita |
| 4,773,087 A | 9/1988 | Plewes |
| 4,819,258 A | 4/1989 | Kleinman et al. |
| 4,821,727 A | 4/1989 | Levene et al. |
| 4,907,156 A | 6/1990 | Doi et al. |
| 4,969,174 A | 11/1990 | Schied |
| 4,989,227 A | 1/1991 | Tirelli et al. |
| 5,018,176 A | 5/1991 | Romeas et al. |
| RE33,634 E | 7/1991 | Yanaki |
| 5,029,193 A | 7/1991 | Saffer |
| 5,051,904 A | 9/1991 | Griffith |
| 5,078,142 A | 1/1992 | Siczek et al. |
| 5,099,846 A | 3/1992 | Hardy |
| 5,129,911 A | 7/1992 | Siczek et al. |
| 5,133,020 A | 7/1992 | Giger et al. |
| 5,163,075 A | 11/1992 | Lubinsky |
| 5,164,976 A | 11/1992 | Scheid et al. |
| 5,199,056 A | 3/1993 | Darrah |
| 5,219,351 A | 6/1993 | Teubner |
| 5,240,011 A | 8/1993 | Assa |
| 5,279,309 A | 1/1994 | Taylor et al. |
| 5,280,427 A | 1/1994 | Magnusson |
| 5,289,520 A | 2/1994 | Pellegrino et al. |
| 5,343,390 A | 8/1994 | Doi et al. |
| 5,359,637 A | 10/1994 | Webbe |
| 5,365,562 A | 11/1994 | Toker |
| 5,386,447 A | 1/1995 | Siczek |
| 5,415,169 A | 5/1995 | Siczek et al. |
| 5,426,685 A | 6/1995 | Pellegrino et al. |
| 5,452,367 A | 9/1995 | Bick |
| 5,491,627 A | 2/1996 | Zhang et al. |
| 5,499,097 A | 3/1996 | Ortyn et al. |
| 5,506,877 A | 4/1996 | Niklason et al. |
| 5,526,394 A | 6/1996 | Siczek |
| 5,539,797 A | 7/1996 | Heidsieck et al. |
| 5,553,111 A | 9/1996 | Moore |
| 5,592,562 A | 1/1997 | Rooks |
| 5,594,769 A | 1/1997 | Pellegrino et al. |
| 5,596,200 A | 1/1997 | Sharma |
| 5,598,454 A | 1/1997 | Franetzki |
| 5,609,152 A | 3/1997 | Pellegrino et al. |
| 5,627,869 A | 5/1997 | Andrew et al. |
| 5,642,433 A | 6/1997 | Lee et al. |
| 5,642,441 A | 6/1997 | Riley et al. |
| 5,647,025 A | 7/1997 | Frost et al. |
| 5,657,362 A | 8/1997 | Giger et al. |
| 5,660,185 A | 8/1997 | Shmulewitz et al. |
| 5,668,889 A | 9/1997 | Hara |
| 5,671,288 A | 9/1997 | Wilhelm et al. |
| 5,712,890 A | 1/1998 | Spivey |
| 5,719,952 A | 2/1998 | Rooks |
| 5,735,264 A | 4/1998 | Siczek et al. |
| 5,763,871 A | 6/1998 | Ortyn et al. |
| 5,769,086 A | 6/1998 | Ritchart et al. |
| 5,773,832 A | 6/1998 | Sayed et al. |
| 5,803,912 A | 9/1998 | Siczek et al. |
| 5,818,898 A | 10/1998 | Tsukamoto et al. |
| 5,828,722 A | 10/1998 | Ploetz |
| 5,835,079 A | 11/1998 | Shieh |
| 5,841,124 A | 11/1998 | Ortyn et al. |
| 5,872,828 A | 2/1999 | Niklason et al. |
| 5,875,258 A | 2/1999 | Ortyn et al. |
| 5,878,104 A | 3/1999 | Ploetz |
| 5,878,746 A | 3/1999 | Lemelson et al. |
| 5,896,437 A | 4/1999 | Ploetz |
| 5,941,832 A | 8/1999 | Tumey |
| 5,954,650 A | 9/1999 | Saito |
| 5,986,662 A | 11/1999 | Argiro |
| 6,005,907 A | 12/1999 | Ploetz |
| 6,022,325 A | 2/2000 | Siczek et al. |
| 6,067,079 A | 5/2000 | Shieh |
| 6,075,879 A | 6/2000 | Roehrig et al. |
| 6,091,841 A | 7/2000 | Rogers |
| 6,101,236 A | 8/2000 | Wang et al. |
| 6,102,866 A | 8/2000 | Nields et al. |
| 6,137,527 A | 10/2000 | Abdel-Malek |
| 6,141,398 A | 10/2000 | He |
| 6,149,301 A | 11/2000 | Kautzer et al. |
| 6,175,117 B1 | 1/2001 | Komardin |
| 6,196,715 B1 | 3/2001 | Nambu |
| 6,215,892 B1 | 4/2001 | Douglass et al. |
| 6,216,540 B1 | 4/2001 | Nelson |
| 6,219,059 B1 | 4/2001 | Argiro |
| 6,256,370 B1 | 4/2001 | Yavus |
| 6,233,473 B1 | 5/2001 | Sheperd |
| 6,243,441 B1 | 6/2001 | Zur |
| 6,245,028 B1 | 6/2001 | Furst et al. |
| 6,272,207 B1 | 8/2001 | Tang |
| 6,289,235 B1 | 9/2001 | Webber et al. |
| 6,292,530 B1 | 9/2001 | Yavus |
| 6,293,282 B1 | 9/2001 | Lemelson |
| 6,327,336 B1 | 12/2001 | Gingold et al. |
| 6,327,377 B1 | 12/2001 | Rutenberg et al. |
| 6,341,156 B1 | 1/2002 | Baetz |
| 6,375,352 B1 | 4/2002 | Hewes |
| 6,389,104 B1 | 5/2002 | Bani-Hashemi et al. |
| 6,411,836 B1 | 6/2002 | Patel |
| 6,415,015 B2 | 7/2002 | Nicolas |
| 6,424,332 B1 | 7/2002 | Powell |
| 6,442,288 B1 | 8/2002 | Haerer |
| 6,459,925 B1 | 10/2002 | Nields et al. |
| 6,463,181 B2 | 10/2002 | Duarte |
| 6,468,226 B1 | 10/2002 | McIntyre, IV |
| 6,480,565 B1 | 11/2002 | Ning |
| 6,501,819 B2 | 12/2002 | Unger et al. |
| 6,556,655 B1 | 4/2003 | Chichereau |
| 6,574,304 B1 | 6/2003 | Hsieh |
| 6,597,762 B1 | 7/2003 | Ferrant |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes |

(56) References Cited

U.S. PATENT DOCUMENTS

| | | |
|---|---|---|
| 6,638,235 B2 | 10/2003 | Miller et al. |
| 6,647,092 B2 | 11/2003 | Eberhard |
| 6,650,928 B1 | 11/2003 | Gailly |
| 6,683,934 B1 | 1/2004 | Zhao |
| 6,744,848 B2 | 6/2004 | Stanton |
| 6,748,044 B2 | 6/2004 | Sabol et al. |
| 6,751,285 B2 | 6/2004 | Eberhard |
| 6,758,824 B1 | 7/2004 | Miller et al. |
| 6,813,334 B2 | 11/2004 | Koppe |
| 6,882,700 B2 | 4/2005 | Wang |
| 6,885,724 B2 | 4/2005 | Li |
| 6,901,156 B2 | 5/2005 | Giger et al. |
| 6,912,319 B1 | 5/2005 | Barnes |
| 6,940,943 B2 | 9/2005 | Claus |
| 6,978,040 B2 | 12/2005 | Berestov |
| 6,987,331 B2 | 1/2006 | Koeppe |
| 6,999,554 B2 | 2/2006 | Mertelmeier |
| 7,022,075 B2 | 4/2006 | Grunwald et al. |
| 7,025,725 B2 | 4/2006 | Dione et al. |
| 7,030,861 B1 | 4/2006 | Westerman |
| 7,110,490 B2 | 9/2006 | Eberhard |
| 7,110,502 B2 | 9/2006 | Tsuji |
| 7,117,098 B1 | 10/2006 | Dunlay et al. |
| 7,123,684 B2 | 10/2006 | Jing et al. |
| 7,127,091 B2 | 10/2006 | OpDeBeek |
| 7,142,633 B2 | 11/2006 | Eberhard |
| 7,218,766 B2 | 5/2007 | Eberhard |
| 7,245,694 B2 | 7/2007 | Jing et al. |
| 7,286,634 B2 | 10/2007 | Sommer, Jr. et al. |
| 7,289,825 B2 | 10/2007 | Fors et al. |
| 7,298,881 B2 | 11/2007 | Giger et al. |
| 7,315,607 B2 | 1/2008 | Ramsauer |
| 7,319,735 B2 | 1/2008 | Defreitas et al. |
| 7,323,692 B2 | 1/2008 | Rowlands |
| 7,346,381 B2 | 3/2008 | Okerlund et al. |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,466,795 B2 | 12/2008 | Eberhard et al. |
| 7,577,282 B2 | 8/2009 | Gkanatsios et al. |
| 7,606,801 B2 * | 10/2009 | Faitelson ............. G06F 21/604 705/64 |
| 7,616,801 B2 | 11/2009 | Gkanatsios et al. |
| 7,630,533 B2 | 12/2009 | Ruth et al. |
| 7,634,050 B2 | 12/2009 | Muller et al. |
| 7,640,051 B2 | 12/2009 | Krishnan |
| 7,697,660 B2 | 4/2010 | Ning |
| 7,702,142 B2 * | 4/2010 | Ren .................. G06T 11/006 378/68 |
| 7,705,830 B2 | 4/2010 | Westerman et al. |
| 7,760,924 B2 * | 7/2010 | Ruth .................. G06T 15/08 382/128 |
| 7,769,219 B2 | 8/2010 | Zahniser |
| 7,787,936 B2 | 8/2010 | Kressy |
| 7,809,175 B2 | 10/2010 | Roehrig et al. |
| 7,828,733 B2 | 11/2010 | Zhang et al. |
| 7,831,296 B2 | 11/2010 | DeFreitas et al. |
| 7,869,563 B2 | 1/2011 | DeFreitas |
| 7,974,924 B2 | 7/2011 | Holla et al. |
| 7,991,106 B2 | 8/2011 | Ren et al. |
| 8,044,972 B2 | 10/2011 | Hall et al. |
| 8,051,386 B2 | 11/2011 | Rosander et al. |
| 8,126,226 B2 | 2/2012 | Bernard et al. |
| 8,155,421 B2 | 4/2012 | Ren et al. |
| 8,165,365 B2 | 4/2012 | Bernard et al. |
| 8,532,745 B2 | 9/2013 | DeFreitas et al. |
| 8,571,289 B2 | 10/2013 | Ruth |
| 8,594,274 B2 | 11/2013 | Hoernig et al. |
| 8,677,282 B2 | 3/2014 | Cragun et al. |
| 8,712,127 B2 | 4/2014 | Ren et al. |
| 8,897,535 B2 | 11/2014 | Ruth et al. |
| 8,983,156 B2 | 3/2015 | Periaswamy et al. |
| 9,020,579 B2 | 4/2015 | Smith |
| 9,075,903 B2 | 7/2015 | Marshall |
| 9,084,579 B2 | 7/2015 | Ren et al. |
| 9,119,599 B2 | 9/2015 | Itai |
| 9,129,362 B2 | 9/2015 | Jerebko |
| 9,289,183 B2 | 3/2016 | Karssemeijer |
| 9,451,924 B2 | 9/2016 | Bernard |
| 9,456,797 B2 | 10/2016 | Ruth et al. |
| 9,478,028 B2 | 10/2016 | Parthasarathy |
| 9,589,374 B1 | 3/2017 | Gao |
| 9,592,019 B2 | 3/2017 | Sugiyama |
| 9,805,507 B2 | 10/2017 | Chen |
| 9,808,215 B2 | 11/2017 | Ruth et al. |
| 9,811,758 B2 | 11/2017 | Ren et al. |
| 9,901,309 B2 | 2/2018 | DeFreitas et al. |
| 10,008,184 B2 | 6/2018 | Kreeger et al. |
| 10,010,302 B2 | 7/2018 | Ruth et al. |
| 10,092,358 B2 | 10/2018 | DeFreitas |
| 10,111,631 B2 | 10/2018 | Gkanatsios |
| 10,242,490 B2 | 3/2019 | Karssemeijer |
| 10,335,094 B2 | 7/2019 | DeFreitas |
| 10,357,211 B2 | 7/2019 | Smith |
| 10,410,417 B2 | 9/2019 | Chen et al. |
| 10,413,263 B2 | 9/2019 | Ruth et al. |
| 10,444,960 B2 | 10/2019 | Marshall |
| 10,456,213 B2 | 10/2019 | DeFreitas |
| 10,573,276 B2 | 2/2020 | Kreeger et al. |
| 10,575,807 B2 | 3/2020 | Gkanatsios |
| 10,595,954 B2 | 3/2020 | DeFreitas |
| 10,624,598 B2 | 4/2020 | Chen |
| 10,977,863 B2 | 4/2021 | Chen |
| 10,978,026 B2 | 4/2021 | Kreeger |
| 11,419,565 B2 | 8/2022 | Gkanatsios |
| 11,508,340 B2 | 11/2022 | Kreeger |
| 2001/0038681 A1 | 11/2001 | Stanton et al. |
| 2001/0038861 A1 | 11/2001 | Hsu et al. |
| 2002/0012450 A1 | 1/2002 | Tsuji |
| 2002/0050986 A1 | 5/2002 | Inoue |
| 2002/0075997 A1 | 6/2002 | Unger et al. |
| 2002/0113681 A1 | 8/2002 | Byram |
| 2002/0122533 A1 | 9/2002 | Marie et al. |
| 2002/0188466 A1 | 12/2002 | Barrette et al. |
| 2002/0193676 A1 | 12/2002 | Bodicker |
| 2003/0007598 A1 | 1/2003 | Wang |
| 2003/0018272 A1 | 1/2003 | Treado et al. |
| 2003/0026386 A1 | 2/2003 | Tang |
| 2003/0048260 A1 | 3/2003 | Matusis |
| 2003/0073895 A1 | 4/2003 | Nields et al. |
| 2003/0095624 A1 | 5/2003 | Eberhard et al. |
| 2003/0097055 A1 | 5/2003 | Yanof |
| 2003/0128893 A1 | 7/2003 | Castorina |
| 2003/0135115 A1 | 7/2003 | Burdette et al. |
| 2003/0169847 A1 | 9/2003 | Karellas |
| 2003/0194050 A1 | 10/2003 | Eberhard |
| 2003/0194121 A1 | 10/2003 | Eberhard et al. |
| 2003/0195433 A1 | 10/2003 | Turovskiy |
| 2003/0210254 A1 | 11/2003 | Doan |
| 2003/0212327 A1 | 11/2003 | Wang |
| 2003/0215120 A1 | 11/2003 | Uppaluri |
| 2004/0008809 A1 | 1/2004 | Webber |
| 2004/0008900 A1 | 1/2004 | Jabri et al. |
| 2004/0008901 A1 | 1/2004 | Avinash |
| 2004/0036680 A1 | 2/2004 | Davis |
| 2004/0047518 A1 | 3/2004 | Tiana |
| 2004/0052328 A1 | 3/2004 | Saboi |
| 2004/0064037 A1 | 4/2004 | Smith |
| 2004/0066884 A1 | 4/2004 | Claus |
| 2004/0066904 A1 | 4/2004 | Eberhard et al. |
| 2004/0070582 A1 | 4/2004 | Smith et al. |
| 2004/0077938 A1 | 4/2004 | Mark et al. |
| 2004/0081273 A1 | 4/2004 | Ning |
| 2004/0094167 A1 | 5/2004 | Brady |
| 2004/0101095 A1 | 5/2004 | Jing et al. |
| 2004/0109028 A1 | 6/2004 | Stern et al. |
| 2004/0109529 A1 | 6/2004 | Eberhard et al. |
| 2004/0127789 A1 | 7/2004 | Ogawa |
| 2004/0138569 A1 | 7/2004 | Grunwald |
| 2004/0171933 A1 | 9/2004 | Stoller et al. |
| 2004/0171986 A1 | 9/2004 | Tremaglio, Jr. et al. |
| 2004/0267157 A1 | 12/2004 | Miller et al. |
| 2005/0047636 A1 | 3/2005 | Gines et al. |
| 2005/0049521 A1 | 3/2005 | Miller et al. |

(56) References Cited

U.S. PATENT DOCUMENTS

| | | |
|---|---|---|
| 2005/0063509 A1 | 3/2005 | Defreitas et al. |
| 2005/0078797 A1 | 4/2005 | Danielsson et al. |
| 2005/0084060 A1 | 4/2005 | Seppi et al. |
| 2005/0089205 A1 | 4/2005 | Kapur |
| 2005/0105679 A1 | 5/2005 | Wu et al. |
| 2005/0107689 A1 | 5/2005 | Sasano |
| 2005/0111718 A1 | 5/2005 | MacMahon |
| 2005/0113680 A1 | 5/2005 | Ikeda et al. |
| 2005/0113681 A1 | 5/2005 | DeFreitas et al. |
| 2005/0113715 A1 | 5/2005 | Schwindt et al. |
| 2005/0124845 A1 | 6/2005 | Thomadsen et al. |
| 2005/0135555 A1 | 6/2005 | Claus |
| 2005/0135664 A1 | 6/2005 | Kaufhold |
| 2005/0226375 A1 | 10/2005 | Eberhard |
| 2006/0009693 A1 | 1/2006 | Hanover et al. |
| 2006/0018526 A1 | 1/2006 | Avinash |
| 2006/0025680 A1 | 2/2006 | Jeune-Iomme |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0132508 A1 | 6/2006 | Sadikali |
| 2006/0147099 A1 | 7/2006 | Marshall et al. |
| 2006/0155209 A1 | 7/2006 | Miller et al. |
| 2006/0197753 A1 | 9/2006 | Hotelling |
| 2006/0210131 A1 | 9/2006 | Wheeler |
| 2006/0228012 A1 | 10/2006 | Masuzawa |
| 2006/0238546 A1 | 10/2006 | Handley |
| 2006/0257009 A1 | 11/2006 | Wang |
| 2006/0269040 A1 | 11/2006 | Mertelmeier |
| 2006/0274928 A1 | 12/2006 | Collins et al. |
| 2006/0291618 A1 | 12/2006 | Eberhard et al. |
| 2007/0019846 A1 | 1/2007 | Bullitt et al. |
| 2007/0030949 A1 | 2/2007 | Jing et al. |
| 2007/0036265 A1 | 2/2007 | Jing et al. |
| 2007/0046649 A1 | 3/2007 | Reiner |
| 2007/0052700 A1 | 3/2007 | Wheeler et al. |
| 2007/0076844 A1 | 4/2007 | Defreitas et al. |
| 2007/0114424 A1 | 5/2007 | Danielsson et al. |
| 2007/0118400 A1 | 5/2007 | Morita et al. |
| 2007/0156451 A1 | 7/2007 | Gering |
| 2007/0223651 A1 | 9/2007 | Wagenaar et al. |
| 2007/0225600 A1 | 9/2007 | Weibrecht et al. |
| 2007/0236490 A1 | 10/2007 | Casteele |
| 2007/0242800 A1 | 10/2007 | Jing et al. |
| 2007/0263765 A1 | 11/2007 | Wu |
| 2007/0274585 A1 | 11/2007 | Zhang et al. |
| 2008/0019581 A1 | 1/2008 | Gkanatsios et al. |
| 2008/0043905 A1 | 2/2008 | Hassanpourgol |
| 2008/0045833 A1 | 2/2008 | DeFreitas et al. |
| 2008/0101537 A1 | 5/2008 | Sendai |
| 2008/0114614 A1 | 5/2008 | Mahesh et al. |
| 2008/0125643 A1 | 5/2008 | Huisman |
| 2008/0130979 A1 | 6/2008 | Ren |
| 2008/0139896 A1 | 6/2008 | Baumgart |
| 2008/0152086 A1 | 6/2008 | Hall |
| 2008/0165136 A1 | 7/2008 | Christie et al. |
| 2008/0187095 A1 | 8/2008 | Boone et al. |
| 2008/0198966 A1 | 8/2008 | Hjarn |
| 2008/0221479 A1 | 9/2008 | Ritchie |
| 2008/0229256 A1 | 9/2008 | Shibaike |
| 2008/0240533 A1 | 10/2008 | Piron et al. |
| 2008/0297482 A1 | 12/2008 | Weiss |
| 2009/0003519 A1 | 1/2009 | DeFreitas et al. |
| 2009/0005668 A1 | 1/2009 | West et al. |
| 2009/0005693 A1 | 1/2009 | Brauner |
| 2009/0010384 A1 | 1/2009 | Jing et al. |
| 2009/0034684 A1 | 2/2009 | Bernard |
| 2009/0037821 A1 | 2/2009 | O'Neal et al. |
| 2009/0079705 A1 | 3/2009 | Sizelove et al. |
| 2009/0080594 A1 | 3/2009 | Brooks et al. |
| 2009/0080602 A1 | 3/2009 | Brooks et al. |
| 2009/0080604 A1 | 3/2009 | Shores et al. |
| 2009/0080752 A1 | 3/2009 | Ruth |
| 2009/0080765 A1 | 3/2009 | Bernard et al. |
| 2009/0087067 A1 | 4/2009 | Khorasani |
| 2009/0123052 A1 | 5/2009 | Ruth |
| 2009/0129644 A1 | 5/2009 | Daw et al. |
| 2009/0135997 A1 | 5/2009 | Defreitas et al. |
| 2009/0138280 A1 | 5/2009 | Morita et al. |
| 2009/0143674 A1 | 6/2009 | Nields |
| 2009/0167702 A1 | 7/2009 | Nurmi |
| 2009/0171244 A1 | 7/2009 | Ning |
| 2009/0238424 A1 | 9/2009 | Arakita |
| 2009/0259958 A1 | 10/2009 | Ban |
| 2009/0268865 A1 | 10/2009 | Ren et al. |
| 2009/0278812 A1 | 11/2009 | Yasutake |
| 2009/0296882 A1 | 12/2009 | Gkanatsios et al. |
| 2009/0304147 A1 | 12/2009 | Jing et al. |
| 2010/0034348 A1 | 2/2010 | Yu |
| 2010/0049046 A1 | 2/2010 | Peiffer |
| 2010/0054400 A1 | 3/2010 | Ren et al. |
| 2010/0079405 A1 | 4/2010 | Bernstein |
| 2010/0086188 A1 | 4/2010 | Ruth et al. |
| 2010/0088346 A1 | 4/2010 | Umess et al. |
| 2010/0098214 A1 | 4/2010 | Star-Lack et al. |
| 2010/0105879 A1 | 4/2010 | Katayose et al. |
| 2010/0121178 A1 | 5/2010 | Krishnan |
| 2010/0131294 A1 | 5/2010 | Venon |
| 2010/0131482 A1 | 5/2010 | Linthicum et al. |
| 2010/0135558 A1 | 6/2010 | Ruth et al. |
| 2010/0152570 A1 | 6/2010 | Navab |
| 2010/0166267 A1 | 7/2010 | Zhang |
| 2010/0195882 A1 | 8/2010 | Ren et al. |
| 2010/0208037 A1 | 8/2010 | Sendai |
| 2010/0231522 A1 | 9/2010 | Li |
| 2010/0246909 A1 | 9/2010 | Blum |
| 2010/0259561 A1 | 10/2010 | Forutanpour et al. |
| 2010/0259645 A1 | 10/2010 | Kaplan |
| 2010/0260316 A1 | 10/2010 | Stein et al. |
| 2010/0280375 A1 | 11/2010 | Zhang |
| 2010/0293500 A1 | 11/2010 | Cragun |
| 2011/0018817 A1 | 1/2011 | Kryze |
| 2011/0019891 A1 | 1/2011 | Puong |
| 2011/0054944 A1 | 3/2011 | Sandberg et al. |
| 2011/0069808 A1 | 3/2011 | Defreitas et al. |
| 2011/0069906 A1 | 3/2011 | Park |
| 2011/0087132 A1 | 4/2011 | DeFreitas et al. |
| 2011/0105879 A1 | 5/2011 | Masumoto |
| 2011/0109650 A1 | 5/2011 | Kreeger |
| 2011/0110570 A1 | 5/2011 | Bar-Shalev |
| 2011/0110576 A1 | 5/2011 | Kreeger |
| 2011/0125526 A1 | 5/2011 | Gustafson |
| 2011/0150447 A1 | 6/2011 | Li |
| 2011/0163939 A1 | 7/2011 | Tam et al. |
| 2011/0178389 A1 | 7/2011 | Kumar et al. |
| 2011/0182402 A1 | 7/2011 | Partain |
| 2011/0234630 A1 | 9/2011 | Batman et al. |
| 2011/0237927 A1 | 9/2011 | Brooks et al. |
| 2011/0242092 A1 | 10/2011 | Kashiwagi |
| 2011/0310126 A1 | 12/2011 | Georgiev et al. |
| 2012/0014504 A1 | 1/2012 | Jang |
| 2012/0014578 A1* | 1/2012 | Karssemeijer ........ G06T 7/0012 382/131 |
| 2012/0069951 A1 | 3/2012 | Toba |
| 2012/0106698 A1 | 5/2012 | Karim |
| 2012/0131488 A1 | 5/2012 | Karlsson et al. |
| 2012/0133600 A1 | 5/2012 | Marshall |
| 2012/0133601 A1 | 5/2012 | Marshall |
| 2012/0134464 A1 | 5/2012 | Hoernig et al. |
| 2012/0148151 A1 | 6/2012 | Hamada |
| 2012/0189092 A1 | 7/2012 | Jerebko |
| 2012/0194425 A1 | 8/2012 | Buelow |
| 2012/0238870 A1 | 9/2012 | Smith et al. |
| 2012/0293511 A1 | 11/2012 | Mertelmeier |
| 2013/0022165 A1 | 1/2013 | Jang |
| 2013/0044861 A1 | 2/2013 | Muller |
| 2013/0059758 A1 | 3/2013 | Haick |
| 2013/0108138 A1 | 5/2013 | Nakayama |
| 2013/0121569 A1 | 5/2013 | Yadav |
| 2013/0121618 A1 | 5/2013 | Yadav |
| 2013/0202168 A1 | 8/2013 | Jerebko |
| 2013/0259193 A1 | 10/2013 | Packard |
| 2014/0033126 A1 | 1/2014 | Kreeger |

(56) References Cited

U.S. PATENT DOCUMENTS

| | | |
|---|---|---|
| 2014/0035811 A1 | 2/2014 | Guehring |
| 2014/0064444 A1 | 3/2014 | Oh |
| 2014/0073913 A1 | 3/2014 | DeFreitas et al. |
| 2014/0200433 A1 | 7/2014 | Choi |
| 2014/0219534 A1 | 8/2014 | Wiemker et al. |
| 2014/0219548 A1 | 8/2014 | Wels |
| 2014/0327702 A1 | 11/2014 | Kreeger et al. |
| 2014/0328517 A1 | 11/2014 | Gluncic |
| 2015/0052471 A1* | 2/2015 | Chen ............ A61B 6/025 715/771 |
| 2015/0061582 A1 | 4/2015 | Smith |
| 2015/0238148 A1 | 8/2015 | Georgescu |
| 2015/0302146 A1 | 10/2015 | Marshall |
| 2015/0309712 A1 | 10/2015 | Marshall |
| 2015/0317538 A1 | 11/2015 | Ren et al. |
| 2015/0331995 A1 | 11/2015 | Zhao |
| 2016/0000399 A1 | 1/2016 | Halmann et al. |
| 2016/0022364 A1 | 1/2016 | DeFreitas et al. |
| 2016/0051215 A1 | 2/2016 | Chen |
| 2016/0078645 A1 | 3/2016 | Abdurahman |
| 2016/0140749 A1 | 5/2016 | Erhard |
| 2016/0228034 A1 | 8/2016 | Gluncic |
| 2016/0235380 A1 | 8/2016 | Smith |
| 2016/0367210 A1 | 12/2016 | Gkanatsios |
| 2017/0071562 A1 | 3/2017 | Suzuki |
| 2017/0262737 A1 | 9/2017 | Rabinovich |
| 2018/0047211 A1 | 2/2018 | Chen et al. |
| 2018/0137385 A1 | 5/2018 | Ren |
| 2018/0144244 A1 | 5/2018 | Masoud |
| 2018/0256118 A1 | 9/2018 | DeFreitas |
| 2019/0015173 A1 | 1/2019 | DeFreitas |
| 2019/0043456 A1 | 2/2019 | Kreeger |
| 2019/0290221 A1 | 9/2019 | Smith |
| 2020/0046303 A1 | 2/2020 | DeFreitas |
| 2020/0093562 A1 | 3/2020 | DeFreitas |
| 2020/0184262 A1 | 6/2020 | Chui |
| 2020/0205928 A1 | 7/2020 | DeFreitas |
| 2020/0253573 A1 | 8/2020 | Gkanatsios |
| 2020/0345320 A1 | 11/2020 | Chen |
| 2020/0390404 A1 | 12/2020 | DeFreitas |
| 2021/0000553 A1 | 1/2021 | St. Pierre |
| 2021/0100518 A1 | 4/2021 | Chui |
| 2021/0100626 A1 | 4/2021 | St. Pierre |
| 2021/0113167 A1 | 4/2021 | Chui |
| 2021/0118199 A1 | 4/2021 | Chui |
| 2022/0005277 A1 | 1/2022 | Chen |
| 2022/0013089 A1 | 1/2022 | Kreeger |
| 2022/0192615 A1 | 6/2022 | Chui |
| 2022/0386969 A1 | 12/2022 | Smith |
| 2023/0033601 A1 | 2/2023 | Chui |
| 2023/0053489 A1 | 2/2023 | Kreeger |
| 2023/0054121 A1 | 2/2023 | Chui |
| 2023/0056692 A1 | 2/2023 | Gkanatsios |
| 2023/0125385 A1 | 4/2023 | Solis |
| 2023/0225821 A1 | 7/2023 | DeFreitas |

FOREIGN PATENT DOCUMENTS

| | | |
|---|---|---|
| CN | 101066212 A | 11/2007 |
| CN | 202161328 | 3/2012 |
| CN | 102429678 | 5/2012 |
| CN | 107440730 | 12/2017 |
| CN | 112561908 A | 3/2021 |
| DE | 102010009295 | 8/2011 |
| DE | 102011087127 | 5/2013 |
| EP | 775467 | 5/1997 |
| EP | 982001 | 3/2000 |
| EP | 1428473 | 6/2004 |
| EP | 2236085 | 6/2010 |
| EP | 2215600 | 8/2010 |
| EP | 2301432 | 3/2011 |
| EP | 2491863 | 8/2012 |
| EP | 1986548 | 1/2013 |
| EP | 2656789 | 10/2013 |
| EP | 2823464 | 1/2015 |
| EP | 2823765 | 1/2015 |
| EP | 3060132 | 4/2019 |
| JP | H09-198490 | 7/1997 |
| JP | H09-238934 | 9/1997 |
| JP | H10-33523 | 2/1998 |
| JP | 2000-200340 | 7/2000 |
| JP | 2002-109510 | 4/2002 |
| JP | 2002-282248 | 10/2002 |
| JP | 2003-189179 | 7/2003 |
| JP | 2003-199737 | 7/2003 |
| JP | 2003-531516 | 10/2003 |
| JP | 2004254742 | 9/2004 |
| JP | 2006-519634 | 8/2006 |
| JP | 2006-312026 | 11/2006 |
| JP | 2007-130487 | 5/2007 |
| JP | 2007-330334 | 12/2007 |
| JP | 2007-536968 | 12/2007 |
| JP | 2008-068032 | 3/2008 |
| JP | 2009-034503 | 2/2009 |
| JP | 2009-522005 | 6/2009 |
| JP | 2009-526618 | 7/2009 |
| JP | 2009-207545 | 9/2009 |
| JP | 2010-137004 | 6/2010 |
| JP | 2011-110175 A | 6/2011 |
| JP | 2012-011255 | 1/2012 |
| JP | 2012-501750 | 1/2012 |
| JP | 2012-061196 | 3/2012 |
| JP | 2013-244211 | 12/2013 |
| JP | 2014-507250 | 3/2014 |
| JP | 2014-534042 | 12/2014 |
| JP | 2015-506794 | 3/2015 |
| JP | 2015-144632 A | 8/2015 |
| JP | 2016-198197 | 12/2015 |
| JP | 2017-056358 | 3/2017 |
| KR | 10-2015-0010515 | 1/2015 |
| KR | 10-2017-0062839 | 6/2017 |
| WO | 90/05485 | 5/1990 |
| WO | 93/17620 | 9/1993 |
| WO | 94/06352 | 3/1994 |
| WO | 1997/00649 | 1/1997 |
| WO | 1998/16903 | 4/1998 |
| WO | 00/51484 | 9/2000 |
| WO | 2003/020114 | 3/2003 |
| WO | 2005051197 | 6/2005 |
| WO | 2005/110230 | 11/2005 |
| WO | 2005110230 | 11/2005 |
| WO | 2005/112767 | 12/2005 |
| WO | 2005112767 | 12/2005 |
| WO | 2006/055830 | 5/2006 |
| WO | 2006/058160 | 6/2006 |
| WO | 2007/095330 | 8/2007 |
| WO | 08/014670 | 2/2008 |
| WO | 2008047270 | 4/2008 |
| WO | 2008/050823 | 5/2008 |
| WO | 2008/054436 | 5/2008 |
| WO | 2009/026587 | 2/2009 |
| WO | 2010/028208 | 3/2010 |
| WO | 2010059920 | 5/2010 |
| WO | 2011008239 | 1/2011 |
| WO | 2011/043838 | 4/2011 |
| WO | 2011065950 | 6/2011 |
| WO | 2011073864 | 6/2011 |
| WO | 2011091300 | 7/2011 |
| WO | 2012/001572 | 1/2012 |
| WO | 2012/068373 | 5/2012 |
| WO | 2012063653 | 5/2012 |
| WO | 2012/112627 | 8/2012 |
| WO | 2012/122399 | 9/2012 |
| WO | 2013/001439 | 1/2013 |
| WO | 2013/035026 | 3/2013 |
| WO | 2013/078476 | 5/2013 |
| WO | 2013/123091 | 8/2013 |
| WO | 2013/136222 | 9/2013 |
| WO | 2014/080215 | 5/2014 |
| WO | 2014/149554 | 9/2014 |
| WO | 2014/207080 | 12/2014 |
| WO | 2015/061582 | 4/2015 |
| WO | 2015/066650 | 5/2015 |

(56) References Cited

FOREIGN PATENT DOCUMENTS

| | | |
|---|---|---|
| WO | 2015/130916 | 9/2015 |
| WO | 2016/103094 | 6/2016 |
| WO | 2016/184746 | 11/2016 |
| WO | 2016/206942 | 12/2016 |
| WO | 2018/183548 | 10/2018 |
| WO | 2018/183549 | 10/2018 |
| WO | 2018/183550 | 10/2018 |
| WO | 2018/236565 | 12/2018 |
| WO | 2021/021329 | 2/2021 |

OTHER PUBLICATIONS

"Supersonic to feature Aixplorer Ultimate at ECR", AuntiMinnie. com, 3 pages (Feb. 2018).
Al Sallab et al., "Self Learning Machines Using Deep Networks", Soft Computing and Pattern Recognition (SoCPaR), 2011 Int'l. Conference of IEEE, Oct. 14, 2011, pp. 21-26.
Berg, WA et al., "Combined screening with ultrasound and mammography vs mammography alone in women at elevated risk of breast cancer", JAMA 299:2151-2163, 2008.
Burbank, Fred, "Stereotactic Breast Biopsy: Its History, Its Present, and Its Future", published in 1996 at the Southeastern Surgical Congress, 24 pages.
Bushberg, Jerrold et al., "The Essential Physics of Medical Imaging", 3rd ed., In: "The Essential Physics of Medical Imaging, Third Edition", Dec. 28, 2011, Lippincott & Wilkins, Philadelphia, PA, USA, XP05579051, pp. 270-272.
Caroline, B.E. et al., "Computer aided detection of masses in digital breast tomosynthesis: A review", 2012 International Conference on Emerging Trends in Science, Engineering and Technology (INCOSET), Tiruchirappalli, 2012, pp. 186-191.
Carton, AK, et al., "Dual-energy contrast-enhanced digital breast tomosynthesis—a feasibility study", Br J Radiol. Apr. 2010;83 (988):344-50.
Chan, Heang-Ping et al., "ROC Study of the effect of stereoscopic imaging on assessment of breast lesions," Medical Physics, vol. 32, No. 4, Apr. 2005, 1001-1009.
Chen, SC, et al., "Initial clinical experience with contrast-enhanced digital breast tomosynthesis", Acad Radio. Feb. 2007 14(2):229-38.
Diekmann, Felix., et al., "Digital mammography using iodine-based contrast media: initial clinical experience with dynamic contrast medium enhancement", Invest Radiol 2005; 40:397-404.
Dromain C., et al., "Contrast enhanced spectral mammography: a multi-reader study", RSNA 2010, 96th Scientific Assembly and Scientific Meeting.
Dromain, C., et al., "Contrast-enhanced digital mammography", Eur J Radiol. 2009; 69:34-42.
Dromain, Clarisse et al., "Dual-energy contrast-enhanced digital mammography: initial clinical results", European Radiology, Sep. 14, 2010, vol. 21, pp. 565-574.
E. Shaw de Paredes et al., "Interventional Breast Procedure", published Sep./Oct. 1998 in Curr Probl Diagn Radiol, pp. 138-184.
EFilm Mobile HD by Merge Healthcare, web site: http://itunes.apple.com/bw/app/efilm-mobile-hd/id405261243?mt=8, accessed on Nov. 3, 2011 (2 pages).
EFilm Solutions, eFilm Workstation (tm) 3.4, website: http://estore.merge.com/na/estore/content.aspx?productID=405, accessed on Nov. 3, 2011 (2 pages).
Ertas, M. et al., "2D versus 3D total variation minimization in digital breast tomosynthesis", 2015 IEEE International Conference on Imaging Systems and Techniques (IST), Macau, 2015, pp. 1-4.
Fischer Imaging Corp, Mammotest Plus manual on minimally invasive breast biopsy system, 2002, 8 pages.
Fischer Imaging Corporation, Installation Manual, MammoTest Family of Breast Biopsy Systems, 86683G, 86684G, P-55957-IM, Issue 1, Revision 3, Jul. 2005, 98 pages.
Fischer Imaging Corporation, Operator Manual, MammoTest Family of Breast Biopsy Systems, 86683G, 86684G, P-55956-OM, Issue 1, Revision 6, Sep. 2005, 258 pages.
Freiherr, G., "Breast tomosynthesis trials show promise", Diagnostic Imaging—San Francisco 2005, V27; N4:42-48.
Georgian-Smith, Dianne, et al., "Stereotactic Biopsy of the Breast Using an Upright Unit, a Vacuum-Suction Needle, and a Lateral Arm-Support System", 2001, at the American Roentgen Ray Society meeting, 8 pages.
Ghiassi, M. et al., "A Dynamic Architecture for Artificial Networks", Neurocomputing, vol. 63, Aug. 20, 2004, pp. 397-413.
Giger et al. "Development of a smart workstation for use in mammography", in Proceedings of SPIE, vol. 1445 (1991), pp. 101103; 4 pages.
Giger et al., "An Intelligent Workstation for Computer-aided Diagnosis", in RadioGraphics, May 1993, 13:3 pp. 647-656; 10 pages.
Hologic, "Lorad StereoLoc II" Operator's Manual 9-500-0261, Rev. 005, 2004, 78 pgs.
Hologic, Inc., 510(k) Summary, prepared Nov. 28, 2010, for Affirm Breast Biopsy Guidance System Special 510(k) Premarket Notification, 5 pages.
Hologic, Inc., 510(k) Summary, prepared Aug. 14, 2012, for Affirm Breast Biopsy Guidance System Special 510(k) Premarket Notification, 5 pages.
ICRP Publication 60: 1990 Recommendations of the International Commission on Radiological Protection, 12 pages.
Jochelson, M., et al, "Bilateral Dual Energy contrast-enhanced digital mammography: Initial Experience", RSNA 2010, 96th Scientific Assembly and Scientific Meeting, 1 page.
Jong, RA, et al., Contrast-enhanced digital mammography: initial clinical experience. Radiology 2003; 228:842-850.
Koechli, Ossi R., "Available Sterotactic Systems for Breast Biopsy", Renzo Brun del Re (Ed.), Minimally Invasive Breast Biopsies, Recent Results in Cancer Research 173:105-113; Springer-Verlag, 2009.
Kopans, et. al. Will tomosynthesis replace conventional mammography? Plenary Session SFN08: RSNA 2005.
Lehman, CD, et al. MRI evaluation of the contralateral breast in women with recently diagnosed breast cancer. N Engl J Med 2007; 356:1295-1303.
Lewin,JM, et al., Dual-energy contrast-enhanced digital subtraction mammography: feasibility. Radiology 2003; 229:261-268.
Lilja, Mikko, "Fast and accurate voxel projection technique in free-form cone-beam geometry with application to algebraic reconstruction," Applies Sciences on Biomedical and Communication Technologies, 2008, Isabel '08, first international symposium on, IEEE, Piscataway, NJ, Oct. 25, 2008.
Lindfors, KK, et al., Dedicated breast CT: initial clinical experience. Radiology 2008; 246(3): 725-733.
Niklason, L., et al., Digital tomosynthesis in breast imaging. Radiology. Nov. 1997; 205(2):399-406.
Pathmanathan et al., "Predicting tumour location by simulating large deformations of the breast using a 3D finite element model and nonlinear elasticity", Medical Image Computing and Computer-Assisted Intervention, pp. 217-224, vol. 3217 (2004).
PCT International Preliminary Report on Patentability in International Application PCT/US2018/024913, mailed Oct. 10, 2019, 8 pages.
PCT International Search Report and Written Opinion in International Application PCT/US2018/024913, mailed Jun. 26, 2018, 10 pages.
Pediconi, "Color-coded automated signal intensity-curve for detection and characterization of breast lesions: Preliminary evaluation of new software for MR-based breast imaging," International Congress Series 1281 (2005) 1081-1086.
Poplack, SP, et al, Digital breast tomosynthesis: initial experience in 98 women with abnormal digital screening mammography. AJR Am J Roentgenology Sep. 2007 189(3):616-23.
Prionas, ND, et al., Contrast-enhanced dedicated breast CT: initial clinical experience. Radiology. Sep. 2010 256(3):714-723.
Rafferty, E. et al., "Assessing Radiologist Performance Using Combined Full-Field Digital Mammography and Breast Tomosynthesis Versus Full-Field Digital Mammography Alone: Results". . . presented at 2007 Radiological Society of North America meeting, Chicago IL.

(56) References Cited

OTHER PUBLICATIONS

Reynolds, April, "Stereotactic Breast Biopsy: A Review", Radiologic Technology, vol. 80, No. 5, Jun. 1, 2009, pp. 447M-464M, XP055790574.
Sakic et al., "Mammogram synthesis using a 3D simulation. I. breast tissue model and image acquisition simulation" Medical Physics. 29, pp. 2131-2139 (2002).
Samani, A. et al., "Biomechanical 3-D Finite Element Modeling of the Human Breast Using MRI Data", 2001, IEEE Transactions on Medical Imaging, vol. 20, No. 4, pp. 271-279.
Shrading, Simone et al., "Digital Breast Tomosynthesis-guided Vacuum-assisted Breast Biopsy: Initial Experiences and Comparison with Prone Stereotactic Vacuum-assisted Biopsy", the Department of Diagnostic and Interventional Radiology, Univ. of Aachen, Germany, published Nov. 12, 2014, 10 pgs.
Smith, A., "Full field breast tomosynthesis", Radiol Manage. Sep.-Oct. 2005; 27(5):25-31.
Van Schie, Guido, et al., "Generating Synthetic Mammograms from Reconstructed Tomosynthesis Volumes", IEEE Transactions on Medical Imaging, vol. 32, No. 12, Dec. 2013, 2322-2331.
Van Schie, Guido, et al., "Mass detection in reconstructed digital breast tomosynthesis volumes with a computer-aided detection system trained on 2D mammograms", Med. Phys. 40(4), Apr. 2013, 41902-1-41902-11.
Weidner N, et al., "Tumor angiogenesis and metastasis: correlation in invasive breast carcinoma", New England Journal of Medicine 1991; 324:1-8.
Weidner, N, "The importance of tumor angiogenesis: the evidence continues to grow", Am J Clin Pathol. Nov. 2004 122(5):696-703.
Wodajo, Felasfa, MD, "Now Playing: Radiology Images from Your Hospital PACS on your iPad," Mar. 17, 2010; web site: http://www.imedicalapps.com/2010/03/now-playing-radiology-images-from-your-hospital-pacs-on-your-ipad/, accessed on Nov. 3, 2011 (3 pages).
Yin, H.M., et al., "Image Parser: a tool for finite element generation from three-dimensional medical images", BioMedical Engineering Online. 3:31, pp. 1-9, Oct. 1, 2004.
Diekmann, Felix et al., "Thick Slices from Tomosynthesis Data Sets: Phantom Study for the Evaluation of Different Algorithms", Journal of Digital Imaging, Springer, vol. 22, No. 5, Oct. 23, 2007, pp. 519-526.
Conner, Peter, "Breast Response to Menopausal Hormone Therapy—Aspects on Proliferation, apoptosis and Mammographic Density", 2007 Annals of Medicine, 39;1, 28-41.
Glick, Stephen J., "Breast CT", Annual Rev. Biomed. Eng., 2007, 9;501-26.
Metheany, Kathrine G. et al., "Characterizing anatomical variability in breast CT images", Oct. 2008, Med. Phys. 35 (10); 4685-4694.
Dromain, Clarisse, et al., "Evaluation of tumor angiogenesis of breast carcinoma using contrast-enhanced digital mammography", AJR: 187, Nov. 2006, 16 pages.
Zhao, Bo, et al., "Imaging performance of an amorphous selenium digital mammography detector in a breast tomosynthesis system", May 2008, Med. Phys 35(5); 1978-1987.
Mahesh, Mahadevappa, "AAPM/RSNA Physics Tutorial for Residents—Digital Mammography: An Overview", Nov.-Dec. 2004, vol. 24, No. 6, 1747-1760.
Zhang, Yiheng et al., "A comparative study of limited-angle cone-beam reconstruction methods for breast tomosythesis", Med Phys., Oct. 2006, 33(10): 3781-3795.
Sechopoulos, et al., "Glandular radiation dose in tomosynthesis of the breast using tungsten targets", Journal of Applied Clinical Medical Physics, vol. 8, No. 4, Fall 2008, 161-171.
Wen, Junhai et al., "A study on truncated cone-beam sampling strategies for 3D mammography", 2004, IEEE, 3200-3204.
Ijaz, Umer Zeeshan, et al., "Mammography phantom studies using 3D electrical impedance tomography with numerical forward solver", Frontiers in the Convergence of Bioscience and Information Technologies 2007, 379-383.
Kao, Tzu-Jen et al., "Regional admittivity spectra with tomosynthesis images for breast cancer detection", Proc. of the 29th Annual Int'l. Conf. of the IEEE EMBS, Aug. 23-26, 2007, 4142-4145.
Varjonen, Mari, "Three-Dimensional Digital Breast Tomosynthesis in the Early Diagnosis and Detection of Breast Cancer", IWDM 2006, LNCS 4046, 152-159.
Taghibakhsh, f. et al., "High dynamic range 2-TFT amplified pixel sensor architecture for digital mammography tomosynthesis", IET Circuits Devices Syst., 2007, 1(10, pp. 87-92.
Chan, Heang-Ping et al., "Computer-aided detection system for breast masses on digital tomosynthesis mammograms: Preliminary Experience", Radiology, Dec. 2005, 1075-1080.
Kopans, Daniel B., "Breast Imaging", 3rd Edition, Lippincott Williams and Wilkins, published Nov. 2, 2006, pp. 960-967.
Williams, Mark B. et al., "Optimization of exposure parameters in full field digital mammography", Medical Physics 35, 2414 (May 20, 2008); doi: 10.1118/1.2912177, pp. 2414-2423.
Elbakri, Idris A. et al., "Automatic exposure control for a slot scanning full field digital mammography system", Med. Phys. 2005; Sep.; 32(9):2763-2770, Abstract only.
Feng, Steve Si Jia, et al., "Clinical digital breast tomosynthesis system: Dosimetric Characterization", Radiology, Apr. 2012, 263(1); pp. 35-42.
Duan, Xiaoman et al., "Matching corresponding regions of interest on cranio-caudal and medio-lateral oblique view mammograms", IEEE Access, vol. 7, Mar. 25, 2019, pp. 31586-31597, XP011715754, DOI: 10.1109/Access.2019.2902854, retrieved on Mar. 20, 2019, abstract.
Samulski, Maurice et al., "Optimizing case-based detection performance in a multiview CAD system for mammography", IEEE Transactions on Medical Imaging, vol. 30, No. 4, Apr. 1, 2011, pp. 1001-1009, XP011352387, ISSN: 0278-0062, DOI: 10.1109/TMI.2011.2105886, abstract.
Nikunjc, Oza et al., Dietterich, T.G., Ed., "Ensemble methods in machine learning", Jan. 1, 2005, Multiple Classifier Systems, Lecture Notes in Computer Science; LNCS, Springer-Verlag Berlin/Heidelberg, pp. 1-15, abstract.

* cited by examiner

SYSTEM AND METHOD FOR TARGETED OBJECT ENHANCEMENT TO GENERATE SYNTHETIC BREAST TISSUE IMAGES

CROSS-REFERENCE TO RELATED APPLICATIONS

This application is a continuation of U.S. patent application Ser. No. 16/497,767, filed Sep. 25, 2019, now U.S. Pat. No. 11,445,993, which is a National Stage Application of PCT/US2018/024913, filed Mar. 28, 2018, which claims priority to and the benefit of U.S. Patent Application Ser. No. 62/479,036, filed Mar. 30, 2017, the disclosures of which are incorporated herein by reference.

FIELD

The presently disclosed inventions relate generally to breast imaging techniques such as tomosynthesis, and more specifically to systems and methods for obtaining, processing, synthesizing, storing and displaying a breast imaging data set or a subset thereof. In particular, the present disclosure relates to implementing one or more target object recognition/synthesis modules to identify respective objects in a tomosynthesis stack, and to combine results from the one or more target object recognition/synthesis modules to generate objects to display in one or more synthesized images.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired image data, and to also provide other benefits. Further, substantial attention and technological development have been dedicated to obtaining three-dimensional images of the breast using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices being mathematically reconstructed on planes typically parallel to the imaging detector. The reconstructed tomosynthesis slices reduce or eliminate the problems caused by tissue overlap and structure noise present in single slice, two-dimensional mammography imaging, by permitting a user (e.g., a radiologist or other medical professional) to scroll through the image slices to view only the structures in that slice.

Imaging systems such as tomosynthesis systems have recently been developed for breast cancer screening and diagnosis. In particular, Hologic, Inc. (www.hologic.com) has developed a fused, multimode mammography/tomosynthesis system that acquires one or both types of mammogram and tomosynthesis images, either while the breast remains immobilized or in different compressions of the breast. Other companies have introduced systems that include tomosynthesis imaging; e.g., which do not include the ability to also acquire a mammogram in the same compression.

Examples of systems and methods that leverage existing medical expertise in order to facilitate, optionally, the transition to tomosynthesis technology are described in U.S. Pat. No. 7,760,924, which is hereby incorporated by reference in its entirety. In particular, U.S. Pat. No. 7,760,924 describes a method of generating a synthesized 2D image, which may optionally be displayed along with tomosynthesis projection or reconstructed images, in order to assist in screening and diagnosis.

The 2D synthesized image is designed to provide a concise representation of the 3D reconstruction slices, including any clinically important and meaningful information, such as abnormal lesions and normal breast structures, while representing in relevant part a traditional 2D image. There are many different types of lesions and breast structures, which may be defined as different types of image objects having different characteristics. For any given image object visible in the 3D volume data, it is important to maintain and enhance the image characteristics (e.g., microcalcifications, architectural distortions, etc.) as much as possible onto the 2D synthesized image. To achieve the enhancement of the targeted image object, it is critical to accurately identify and represent the image object present in the 3D tomosynthesis data.

SUMMARY

In one embodiment of the disclosed inventions, a method for processing breast tissue image data includes obtaining image data of a patient's breast tissue, processing the image data to generate a set of image slices, the image slices collectively depicting the patient's breast tissue; feeding image slices of the set through each of a plurality of object-recognizing modules, each of the object-recognizing modules being configured to recognize a respective type of object that may be present in the image slices; combining objects recognized by the respective object-recognizing modules to generate a synthesized image of the patient's breast tissue; and displaying the synthesized image.

These and other aspects and embodiments of the disclosed inventions are described in more detail below, in conjunction with the accompanying figures.

BRIEF DESCRIPTION OF THE FIGURES

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
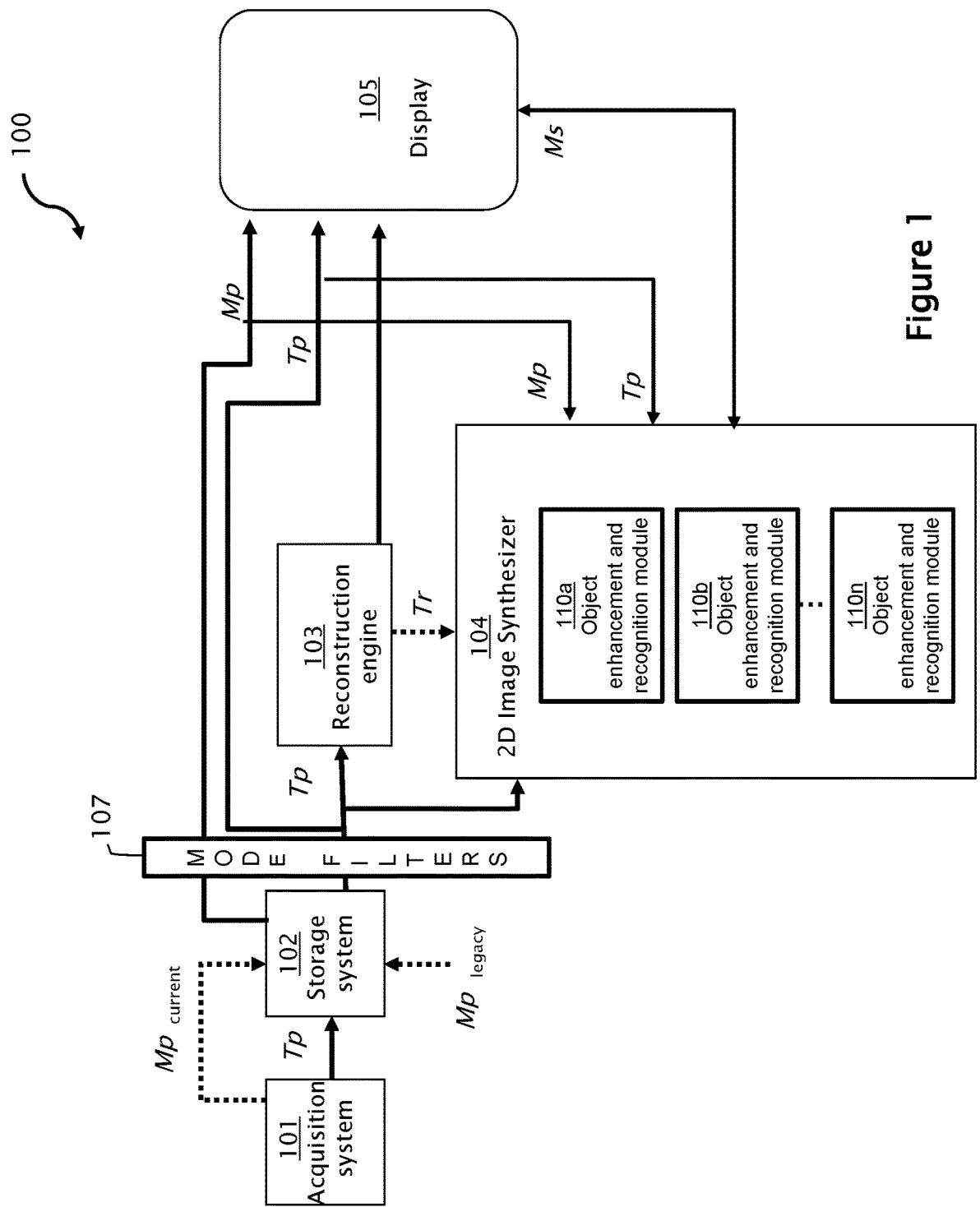
FIG. 1 is a block diagram illustrating the flow of data through an exemplary breast image acquisition and processing system in accordance with embodiments of the disclosed inventions.

All numeric values are herein assumed to be modified by the terms "about" or "approximately," whether or not explicitly indicated, wherein the terms "about" and "approximately" generally refer to a range of numbers that one of skill in the art would consider equivalent to the recited value (i.e., having the same function or result). In some instances, the terms "about" and "approximately" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the disclosed inventions, which is defined only by the appended claims and their equivalents. In addition, an illustrated embodiment of the disclosed inventions needs not have all the aspects or advantages shown. For example, an aspect or an advantage described in conjunction with a particular embodiment of the disclosed inventions is not necessarily limited to that embodiment and can be practiced in any other embodiments even if not so illustrated.

For the following defined terms and abbreviations, these definitions shall be applied throughout this patent specification and the accompanying claims, unless a different definition is given in the claims or elsewhere in this specification:

An "acquired image" refers to an image generated while visualizing a patient's tissue. Acquired images can be generated by radiation from a radiation source impacting on a radiation detector disposed on opposite sides of a patient's tissue, as in a conventional mammogram.

A "reconstructed image" refers to an image generated from data derived from a plurality of acquired images. A reconstructed image simulates an acquired image not included in the plurality of acquired images.

A "synthesized image" refers to an artificial image generated from data derived from a plurality of acquired and/or reconstructed images. A synthesized image includes elements (e.g., objects and regions) from the acquired and/or reconstructed images, but does not necessarily correspond to an image that can be acquired during visualization. Synthesized images are constructed analysis tools.

An "Mp" image is a conventional mammogram or contrast enhanced mammogram, which are two-dimensional (2D) projection images of a breast, and encompasses both a digital image as acquired by a flat panel detector or another imaging device, and the image after conventional processing to prepare it for display (e.g., to a health professional), storage (e.g., in the PACS system of a hospital), and/or other use.

A "Tp" image is an image that is similarly two-dimensional (2D), but is acquired at a respective tomosynthesis angle between the breast and the origin of the imaging x rays (typically the focal spot of an x-ray tube), and encompasses the image as acquired, as well as the image data after being processed for display, storage, and/or other use.

A "Tr" image is a type (or subset) of a reconstructed image that is reconstructed from tomosynthesis projection images Tp, for example, in the manner described in one or more of U.S. Pat. Nos. 7,577,282, 7,606,801, 7,760,924, and 8,571,289, the disclosures of which are fully incorporated by reference herein in their entirety, wherein a Tr image represents a slice of the breast as it would appear in a projection x ray image of that slice at any desired angle, not only at an angle used for acquiring Tp or Mp images.

An "Ms" image is a type (or subset) of a synthesized image, in particular, a synthesized 2D projection image that simulates mammography images, such as a craniocaudal (CC) or mediolateral oblique (MLO) images, and is constructed using tomosynthesis projection images Tp, tomosynthesis reconstructed images Tr, or a combination thereof. Ms images may be provided for display to a health professional or for storage in the PACS system of a hospital or another institution. Examples of methods that may be used to generate Ms images are described in the above-incorporated U.S. Pat. Nos. 7,760,924 and 8,571,289.

It should be appreciated that Tp, Tr, Ms and Mp image data encompasses information, in whatever form, that is sufficient to describe the respective image for display, further processing, or storage. The respective Mp, Ms. Tp and Tr images are typically provided in digital form prior to being displayed, with each image being defined by information that identifies the properties of each pixel in a two-dimensional array of pixels. The pixel values typically relate to respective measured, estimated, or computed responses to X-rays of corresponding volumes in the breast, i.e., voxels or columns of tissue. In a preferred embodiment, the geometry of the tomosynthesis images (Tr and Tp) and mammography images (Ms and Mp) are matched to a common coordinate system, as described in U.S. Pat. No.

7,702,142. Unless otherwise specified, such coordinate system matching is assumed to be implemented with respect to the embodiments described in the ensuing detailed description of this patent specification.

The terms "generating an image" and "transmitting an image" respectively refer to generating and transmitting information that is sufficient to describe the image for display. The generated and transmitted information is typically digital information.

In order to ensure that a synthesized 2D image displayed to an end-user (e.g., an Ms image) includes the most clinically relevant information, it is necessary to detect and identify three-dimensional (3D) objects, such as malignant breast mass, tumors, etc., within the breast tissue. Towards this end, in accordance with embodiments of the presently disclosed inventions, 3D objects may be identified using multiple target object recognition/synthesis modules, wherein each target recognition/synthesis module may be configured to identify and reconstruct a particular type of object. These multiple target synthesis modules may work together in combining information pertaining to respective objects during the reconstruction process of generating one or more synthesized 2D images, ensuring that each object is represented accurately, and preserving clinically significant information on the 2D synthesized images that are the displayed to the end-user.

FIG. 1 illustrates the flow of data in an exemplary image generation and display system 100, which incorporates each of synthesized image generation, object identification, and display technology. It should be understood that, while FIG. 1 illustrates a particular embodiment of a flow diagram with certain processes taking place in a particular serial order or in parallel, the claims and various other embodiments described herein are not limited to the performance of the image processing steps in any particular order, unless so specified.

More particularly, the image generation and display system 100 includes an image acquisition system 101 that acquires tomosynthesis image data for generating Tp images of a patient's breasts, using the respective three-dimensional and/or tomosynthesis acquisition methods of any of the currently available systems. If the acquisition system is a combined tomosynthesis/mammography system, Mp images may also be generated. Some dedicated tomosynthesis systems or combined tomosynthesis/mammography systems may be adapted to accept and store legacy mammogram images, (indicated by a dashed line and legend "$Mp_{legacy}$" in FIG. 1) in a storage device 102, which is preferably a DICOM-compliant Picture Archiving and Communication System (PACS) storage device. Following acquisition, the tomosynthesis projection images Tp may also be transmitted to the storage device 102 (as shown in FIG. 1). The storage device 102 may further store a library of known 3D objects that may be used to identify significant 3D image patterns to the end-user. In other embodiments, a separate dedicated storage device (not shown) may be used to store the library of known 3D objects with which to identify 3D image patterns or objects.

The Tp images are transmitted from either the acquisition system 101, or from the storage device 102, or both, to a computer system configured as a reconstruction engine 103 that reconstructs the Tp images into reconstructed image "slices" Tr, representing breast slices of selected thickness and at selected orientations, as disclosed in the above-incorporated patents and applications.

Mode filters 107 are disposed between image acquisition and image display. The filters 107 may additionally include customized filters for each type of image (i.e., Tp, Mp, and Tr images) arranged to identify and highlight certain aspects of the respective image types. In this manner, each imaging mode can be tuned or configured in an optimal way for a specific purpose. For example, filters programmed for recognizing objects across various 2D image slices may be applied in order to detect image patterns that may belong to a particular high-dimensional objects. The tuning or configuration may be automatic, based on the type of the image, or may be defined by manual input, for example through a user interface coupled to a display. In the illustrated embodiment of FIG. 1, the mode filters 107 are selected to highlight particular characteristics of the images that are best displayed in respective imaging modes, for example, geared towards identifying objects, highlighting masses or calcifications, identifying certain image patterns that may be constructed into a 3D object, or for creating 2D synthesized images (described below). Although FIG. 1 illustrates only one mode filter 107, it should be appreciated that any number of mode filters may be utilized in order to identify structures of interest in the breast tissue.

The imaging and display system 100 further includes a 2D image synthesizer 104 that operates substantially in parallel with the reconstruction engine 103 for generating 2D synthesized images using a combination of one or more Tp, Mp, and/or Tr images. The 2D image synthesizer 104 consumes a set of input images (e.g., Mp, Tr and/or Tp images), determines a set of most relevant features from each of the input images, and outputs one or more synthesized 2D images. The synthesized 2D image represents a consolidated synthesized image that condenses significant portions of various slices onto one image. This provides an end-user (e.g., medical personnel, radiologist, etc.) with the most clinically-relevant image data in an efficient manner, and reduces time spent on other images that may not have significant data.

One type of relevant image data to highlight in the synthesized 2D images would be relevant objects found across one or more Mp, Tr and/or Tp images. Rather than simply assessing image patterns of interest in each of the 2D image slices, it may be helpful to determine whether any of the 2D image patterns of interest belong to a larger high-dimensional structure, and if so, to combine the identified 2D image patterns into a higher-dimensional structure. This approach has several advantages, but in particular, by identifying high-dimensional structures across various slices/depths of the breast tissue, the end-user may be better informed as to the presence of a potentially significant structure that may not be easily visible in various 2D slices of the breast.

Further, instead of identifying similar image patterns in two 2D slices (that are perhaps adjacent to each other), and determining whether or not to highlight image data from one or both of the 2D slices, identifying both image patterns as belonging to the same high-dimensional structure may allow the system to make a more accurate assessment pertaining to the nature of the structure, and consequently provide significantly more valuable information to the end-user. Also, by identifying the high-dimensional structure, the structure can be more accurately depicted on the synthesized 2D image. Yet another advantage of identifying high-dimensional structures within the various captured 2D slices of the breast tissue relates to identifying a possible size/scope of the identified higher-dimensional structure. For example, once a structure has been identified, previously unremarkable image patterns that are somewhat proximate to the high-dimensional structure may now be identified as belonging to the same structure. This may provide the end-user with an indication that the high-dimensional structure is increasing in size/scope.

To this end, the 2D image synthesizer 104 employs a plurality of target object recognition/enhancement modules (also referred to as target object synthesis modules) that are configured to identify and reconstruct different types of objects. Each target image recognition/synthesis module may be applied (or "run") on a stack (e.g., a tomosynthesis image stack) of 2D image slices of a patient's breast tissue, and work to identify particular types of objects that may be in the breast tissue, and ensure that such object(s) are represented in a clinically-significant manner in the resulting 2D synthesized image presented to the end-user. For example, a first target image synthesis module may be configured to identify calcifications in the breast tissue. Another target image synthesis module may be configured to identify and reconstruct spiculated lesions in the breast tissue. Yet another target image synthesis module may be configured to identify and reconstruct spherical masses in the breast tissue. In one or more embodiments, the multiple target image synthesis modules process the image slice data and populate respective objects in a high-dimensional grid (e.g., 3D grid) comprising respective high-dimensional structures (e.g., 3D objects) present in the breast tissue. This high-dimensional grid may then be utilized to accurately depict the various structures in the 2D synthesized image.

A high-dimensional object may refer to any object that comprises at least three or more dimensions, e.g., 3D or higher object, or a 3D or higher object and time dimension, etc. Examples of such objects or structures include, without limitation, calcifications, spiculated lesions, benign tumors, irregular masses, dense objects, etc. An image object may be defined as a certain type of image pattern that exists in the image data. The object may be a simple round object in a 3D space, and a corresponding flat round object in a 2D space. It can be an object with complex patterns and complex shapes, and it can be of any size or dimension. The concept of an object may extend past a locally bound geometrical object. Rather, the image object may refer to an abstract pattern or structure that can exist in any dimensional shape. It should be appreciated that the inventions disclosed herein are not limited to 3D objects and/or structures, and may include higher-dimensional structures. It should be appreciated that each of the target image synthesis modules is configured for identifying and reconstructing respective types of objects. These "objects" may refer to 2D shapes, 2D image patterns, 3D objects, or any other high-dimensional object, but in any event will all be referred to as "objects" or "3D objects" herein for simplicity, but this illustrative use should not be otherwise read as limiting the scope of the claims.

In the illustrated embodiment, the 2D synthesizer 104 comprises a plurality of target object recognition/enhancement modules (e.g., 110a, 110b . . . 110n), each configured for recognizing and enhancing a particular type of object. Each of the target object recognition/enhancement modules 110 may be run on a 2D image stack (e.g., Tr image stack), and is configured to identify the respective object (if any is/are present) therein. By identifying the assigned object in the 2D image stack, each target object recognition/enhancement module 110 works to ensure that the respective object is preserved and depicted accurately in the resulting 2D synthesized image presented to the end-user.

In some embodiments, a hierarchical model may be utilized in determining which objects to emphasize or de-emphasize in the 2D synthesized image based on a weight or priority assigned to the target object recognition/enhancement module. In other embodiments, all objects may be treated equally, and different objects may be fused together if there is an overlap in the z direction, as will be discussed in further detail below. These reconstruction techniques allow for creation of 2D synthesized images that comprise clinically-significant information, while eliminating or reducing unnecessary or visually confusing information.

The synthesized 2D images may be viewed at a display system 105. The reconstruction engine 103 and 2D image synthesizer 104 are preferably connected to a display system 105 via a fast transmission link. The display system 105 may be part of a standard acquisition workstation (e.g., of acquisition system 101), or of a standard (multi-display) review station (not shown) that is physically remote from the acquisition system 101. In some embodiments, a display connected via a communication network may be used, for example, a display of a personal computer or of a so-called tablet, smart phone or other hand-held device. In any event, the display 105 of the system is preferably able to display respective Ms, Mp, Tr, and/or Tp images concurrently, e.g., in separate side-by-side monitors of a review workstation, although the invention may still be implemented with a single display monitor, by toggling between images.

Thus, the imaging and display system 100, which is described as for purposes of illustration and not limitation, is capable of receiving and selectively displaying tomosynthesis projection images Tp, tomosynthesis reconstruction images Tr, synthesized mammogram images Ms, and/or mammogram (including contrast mammogram) images Mp, or any one or sub combination of these image types. The system 100 employs software to convert (i.e., reconstruct) tomosynthesis images Tp into images Tr, software for synthesizing mammogram images Ms, software for decomposing 3D objects, software for creating feature maps and object maps. An object of interest or feature in a source image may be considered a 'most relevant' feature for inclusion in a 2D synthesized image based upon the application of the object maps along with one or more algorithms and/or heuristics, wherein the algorithms assign numerical values, weights or thresholds, to pixels or regions of the respective source images based upon identified/detected objects and features of interest within the respective region or between features. The objects and features of interest may include, for example, spiculated lesions, calcifications, and the like.

Figure 2:
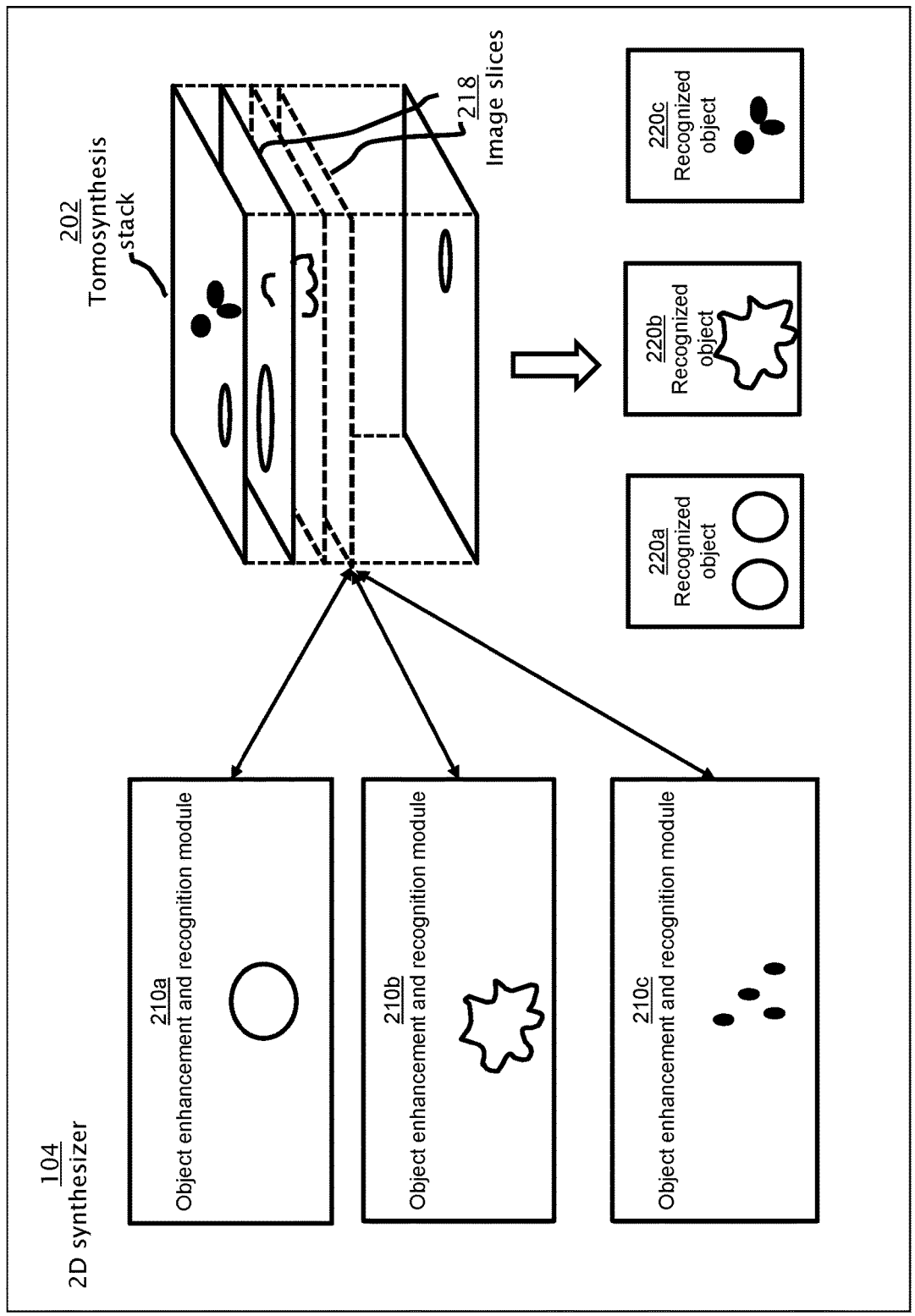
FIG. 2 is a block diagram illustrating the flow of data through a 2D synthesizer that utilizes multiple target object recognition/enhancement modules to identify respective objects in an image stack in accordance with embodiments of the disclosed inventions.

FIG. 2 illustrates the 2D image synthesizer 104 in further detail. As discussed above, various image slices 218 of a tomosynthesis data set (or "stack") 202 (e.g., filtered and/or unfiltered Mp, Tr and/or Tp images of a patient's breast tissue) are input into the 2D image synthesizer 104, and then processed to determine portions of the images to highlight in a synthesized 2D image that will be displayed on the display 105. The image slices 218 may be consecutively-captured cross-sections of a patient's breast tissue. Or, the image slices 218 may be cross-sectional images of the patient's breast tissue captured at known intervals. The tomosynthesis image stack 202 comprising the image slices 218 may be forwarded to the 2D image synthesizer 104, which evaluates each of the source images in order to (1) identify various types of objects (Tr) for possible inclusion in one or more 2D synthesized images, and/or (2) identify respective pixel regions in the images that contain the identified objects.

As shown in the illustrated embodiment, the tomosynthesis stack 202 comprises a plurality of images 218 taken at various depths/cross-sections of the patient's breast tissue. Some of the images 218 in the tomosynthesis stack 202 comprise 2D image patterns. Thus, the tomosynthesis stack 202 comprises a large number of input images containing various image patterns within the images of the stack.

More particularly, as shown in FIG. 2, three target object recognition/enhancement modules 210a, 210b and 210c are configured to run on the tomosynthesis stack 202, wherein each of the target object recognition and enhancement modules 210 corresponds to a respective set of programs/rules and parameters that define a particular object, and how to identify that particular object amongst other objects that may exist in the breast tissue depicted by the tomosynthesis stack 202. For example, filtering/image recognition techniques and various algorithms/heuristics may be run on the tomosynthesis stack 202 in order to identify the object assigned to the particular target object recognition/enhancement module 210. It will be appreciated that there are many ways to recognize objects using a combination of image manipulation/filtration techniques.

For the purposes of illustration, it will be assumed that the each of the target object recognition/enhancement modules 210 identifies at least one respective object, but it should be appreciated that in many cases no objects will be identified. However, even healthy breast tissue may have one or more suspicious objects or structures, and the target object recognition/enhancement modules may inadvertently identify a breast background object. For example, all breast linear tissue and density tissue structures can be displayed as the breast background object. In other embodiments, "healthy" objects such as spherical shapes, oval shapes, etc., may simply be identified by one or more of the target object recognition/enhancement modules 210. The identified 3D objects may then be displayed on the 2D synthesized image 206; of course, out of all identified 2D objects, more clinically-significant objects may be prioritized/enhanced when displaying the respective objects on the 2D synthesized image, as will be discussed in further detail below.

In the illustrated embodiment, a first target object recognition/enhancement module 210a is configured to recognize circular and/or spherical shapes in the images 218 of the tomosynthesis stack 202 (e.g., Tr, Tp, Mp, etc.). A second target object synthesis module 210b is configured to recognize lobulated shapes. A third target object synthesis module 210c is configured to recognize calcification patterns. In particular, each of the target object synthesis modules 210a, 210b and 210c is run on the Tr image stack 202, wherein a set of features/objects are recognized by the respective target object synthesis modules.

For example, target object recognition/enhancement module 210a may recognize one or more circular shapes and store these as "recognized objects" 220a. It will be appreciated that multiple image slices 218 of the stack 202 may contain circular shapes, and that these shapes may be associated with the same spherical object, or may belong to different spherical objects. In the illustrated embodiment, at least two distinct circular objects are recognized by the target object recognition/enhancement module 210a.

Similarly, target object recognition/enhancement module 210b may recognize one or more lobulated shapes and store these as recognized objects 220b. In the illustrated embodiment, one lobulated object has been recognized in the tomosynthesis stack 202 by the target object recognition/enhancement module 210b. As can be seen, two different image slices 218 in the tomosynthesis stack 202 depict portions of the lobulated object, but the respective portions are recognized as belonging to a single lobulated object by the recognition/enhancement module 210b, and stored as a single recognized object 220b.

Finally, target object recognition/enhancement module 210c may recognize one or more calcification shapes and store these as recognized objects 220c. In the illustrated embodiment, a (single) calcification cluster has been recognized by the target object recognition/enhancement module 210c and stored as a recognized object 220c. The recognized objects 220a, 220b and 220c may be stored at storage facilities corresponding to the respective target object recognition/enhancement modules 210a, 210b and 210c, or alternatively at a separate (i.e., single) storage facility that may be accessed by each of the target object recognition/enhancement modules.

Figure 3:
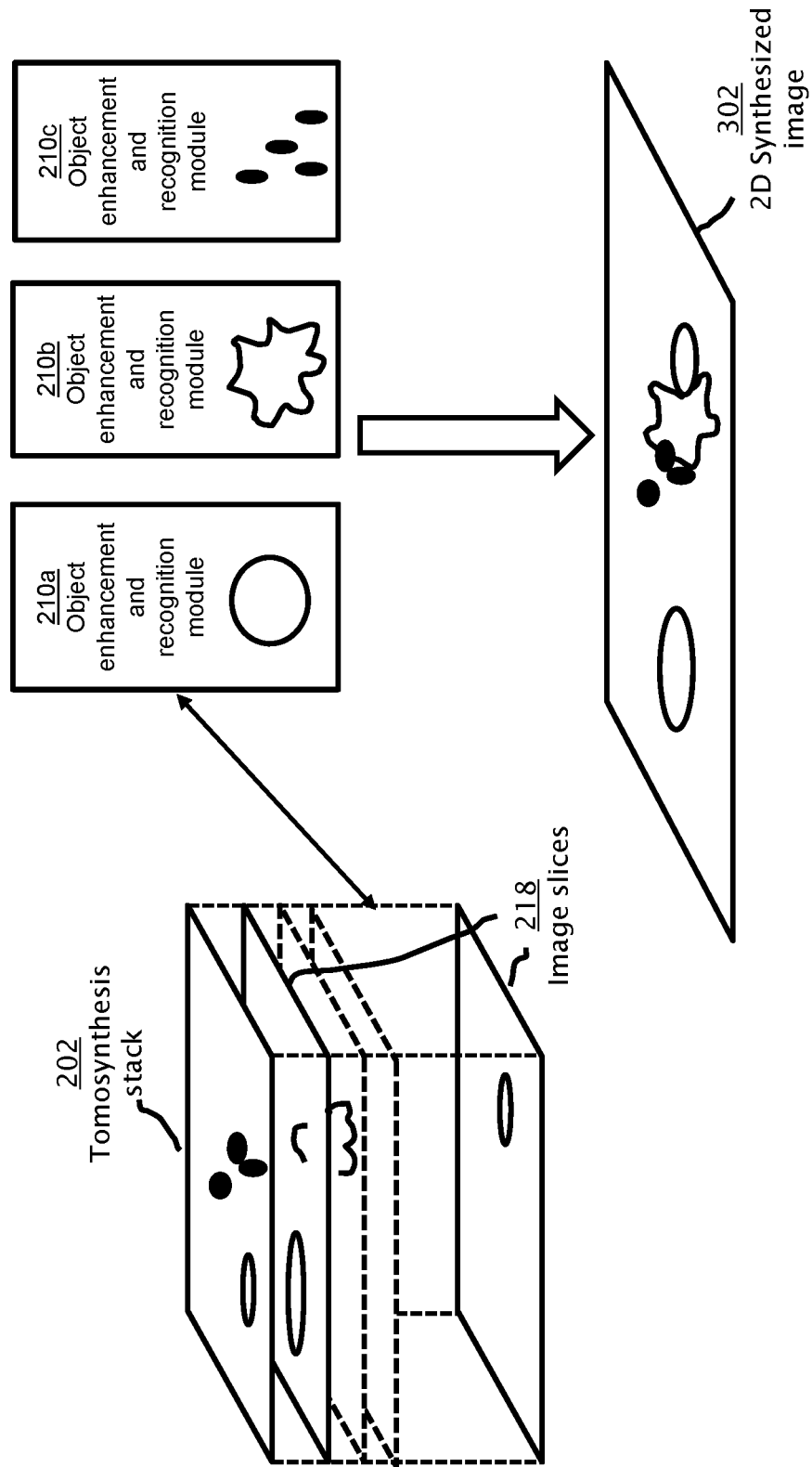
FIG. 3 illustrates one embodiment of applying target object recognition/enhancement modules on an image stack to recognize respective objects and reduce the objects onto the 2D synthesized image.

Referring now to FIG. 3, each of the target object recognition/enhancement modules 210 may be configured to identify and synthesize (e.g., to reduce to 2D) a respective 3D object to be displayed on the one or more 2D synthesized images. In other words, once the 3D objects are recognized by the respective target object recognition/enhancement module 210a, 210b or 210c, the target object recognition/enhancement module thereafter converts the recognized 3D object into a 2D format so that the recognized object may be displayed on the 2D synthesized image. In the illustrated embodiment, the target object recognition/enhancement modules 210a, 21b and 210c recognize respective objects, and convert the recognized objects into respective 2D formats. As part of the conversion process, certain of the recognized objects may be enhanced to a greater or lesser degree for the displayed image, as will be discussed in further detail below. Assuming all three target object recognition/enhancement modules 210a, 210b and 210c are considered equally important to the 2D image synthesizer 104, the respective 2D formats of all recognized objects (e.g., two spherical objects, one lobular object, and one calcification mass) depicted on the 2D synthesized image 302.

Figure 4:
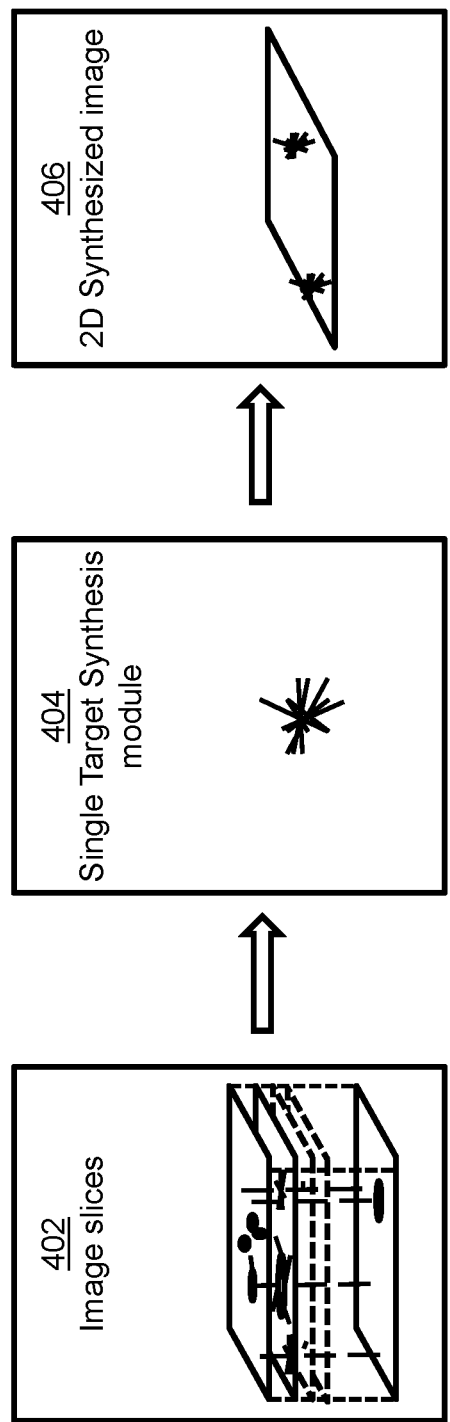
FIG. 4 illustrates a flow of data when applying a single target object recognition/enhancement module on an image stack.

FIG. 4 illustrates how a single target object recognition/enhancement module 210 may be run on a tomosynthesis stack to generate a portion of the 2D synthesized image. In the illustrated embodiment, image slices 402 are fed through a single target object recognition/enhancement module 404, which is configured to recognize star shaped objects in the stack of images 402. As a result, the single target object synthesis module reduces information pertaining to the recognized star shape gained from various depths of the image slices onto a single 2D synthesized image 406.

Figure 5:
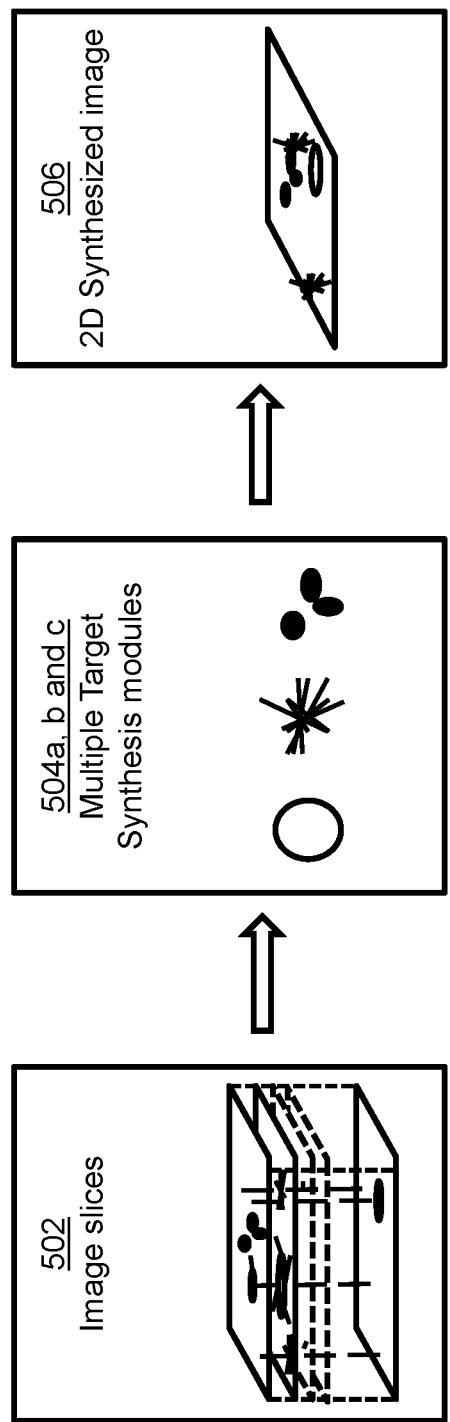
FIG. 5 illustrates a flow of data when applying multiple target object recognition/enhancement modules on an image stack.

FIG. 5 illustrates an exemplary embodiment for having multiple target object recognition/enhancement modules work together to produce the 2D synthesized image. In the illustrated embodiment, image slices 502 (of a respective stack) are fed through a first target object recognition/enhancement module 504a configured to recognize and reconstruct circular and/or spherical shapes, a second target object recognition/enhancement module 504b configured to recognize and reconstruct star-like shapes, and a third target object recognition/enhancement module 504c configured to recognize and reconstruct calcification structures. It should be appreciated that any number of target object recognition/enhancement modules may be programmed for any number of object types.

Each of the target object recognition/enhancement modules 504a, 504b and 504c corresponds to respective algorithms that are configured with various predetermined rules and attributes that enable these programs to successfully recognize respective objects, and reduce the recognized objects to a 2D format. By applying all three target object recognition/synthesis modules 504a, 504b and 504c to the image slices 502, a 2D synthesized image 506 is generated. In particular, rather than simply displaying a single type of object, the 2D synthesized image 506 comprises all three object types that are recognized and synthesized by the three target object recognition/enhancement modules 504a, 504b and 504c, with each of the recognized objects being equally emphasized. While this may be desirable if all the object types are of equal significance, it may be helpful to enhance/emphasize different object types to varying degrees based on their weight/priority. This technique may be more effective in alerting the end-user to a potentially important object, while de-emphasizing objects of lesser importance.

Figure 6A:
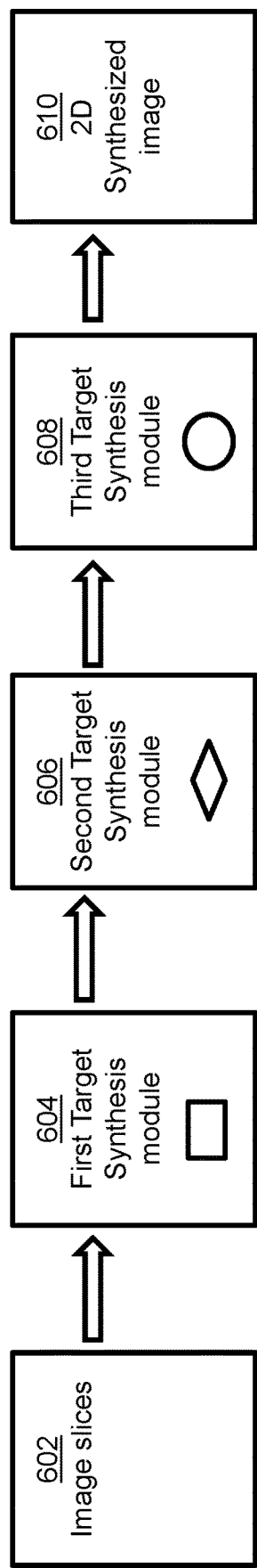
FIGS. 6A and 6B illustrate a sequential combination technique of combining data from multiple target object synthesis modules.

Referring now to FIG. 6A, a hierarchical sequential approach to combine data from the multiple target object recognition/enhancement modules is illustrated. In particular, a sequential combination technique may be applied if the various object types have a clearly defined hierarchy associated with them. For example, one type of object (e.g., spiculated lesions) may be deemed to be more clinically significant than another type of object (e.g., a spherical mass in breast tissue). This type of object (and the corresponding target object module) may be assigned a particular high weight/priority. In such a case, if two objects are competing for space on the 2D synthesized image, the object type associated with the higher priority may be emphasized/displayed on the 2D synthesized image, and the other object type may be de-emphasized, or not displayed at all. Similarly, in such an approach, each of the target object recognition/enhancement modules may be assigned respective weights based on respective significance.

In the illustrated embodiment, the image slices 602 are sequentially fed through three different target object recognition/enhancement modules (604, 606 and 608) to generate the 2D synthesized image 610, wherein each of the target object synthesis modules is configured to recognize and reconstruct a particular type of object. The first target object recognition/enhancement module 604 (associated with a square-shaped object) is run first on the reconstruction image slices 602, followed by the second target object recognition/enhancement module 606 (associated with a diamond-shaped object), and then followed by the third target object recognition/enhancement module 608 (associated with a circular-shaped object). It should be appreciated that since the target object recognition/enhancement modules are applied (or "run") sequentially, the second target object recognition/enhancement module 606 may be considered a higher priority object as compared with the first target object recognition/enhancement module 604, and the third target object recognition/enhancement module 608 may be considered as having a higher priority as compared to the second target object recognition/enhancement module 606. Thus, the third object type may override (or be emphasized over) the second object type, and the second object type may override (or be emphasized over) the first object type.

Figure 6B:
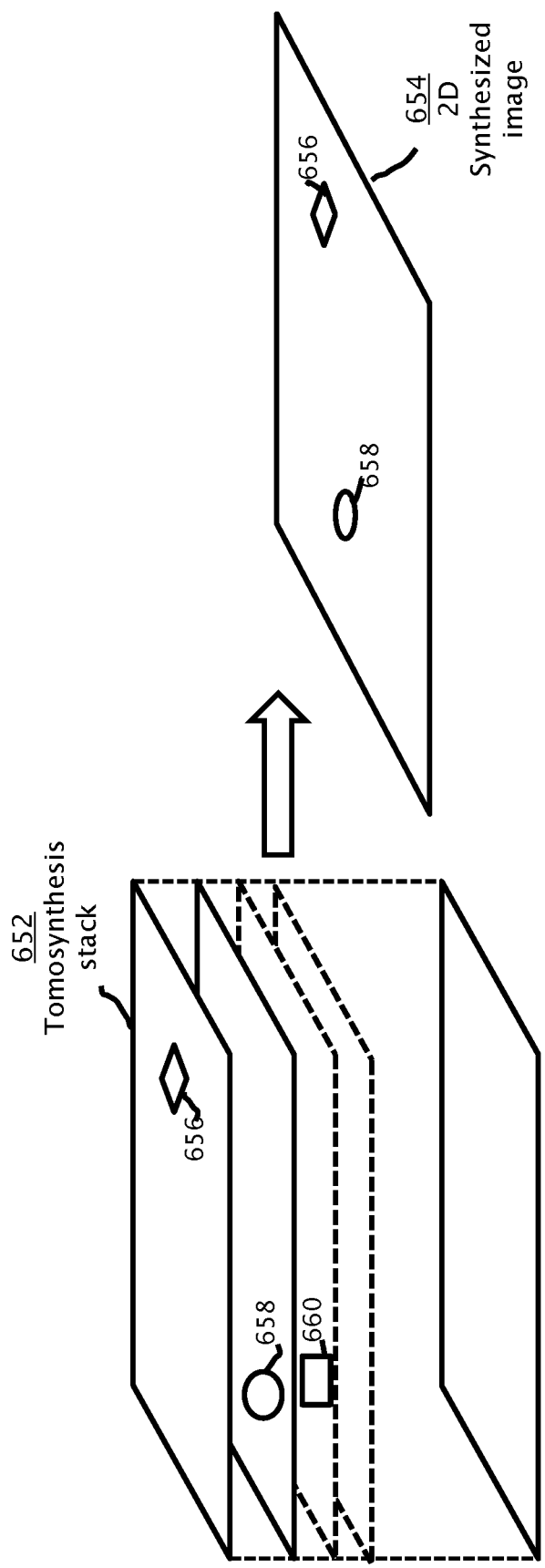

FIG. 6B illustrates this hierarchical approach to combining various object types sequentially. In particular, the tomosynthesis image stack 652 includes objects 656, 658 and 660 that can be recognized in various image slices. As illustrated, objects 658 and 660 somewhat overlap in the z direction, which means that they are likely to compete for representation in the 2D synthesized image 654. When using the sequential approach of FIG. 6A to combine data from the multiple target object recognition/enhancement modules 604, 606 and 608, the programmed hierarchy is preserved. Thus, since target object recognition/enhancement module 608 configured to recognize and reconstruct circular-shaped objects has higher priority as compared to target object recognition/enhancement module 604 configured to recognize and reconstruct square-shaped objects, in a case of overlap between the two objects (as is the case in FIG. 6B), circular-shaped object 658 overrides square-shaped object 660 in the 2D synthesized image 654. Of course, it should be appreciated that since diamond-shaped object 656 does not overlap in the z direction with the other two objects, diamond shaped object 656 is also displayed in the 2D synthesized image 654. In other embodiments, instead of completing overriding the lower-priority object, the object with high-priority may be emphasized relative to the lower-priority object (rather than be omitted from display).

Figure 7A:
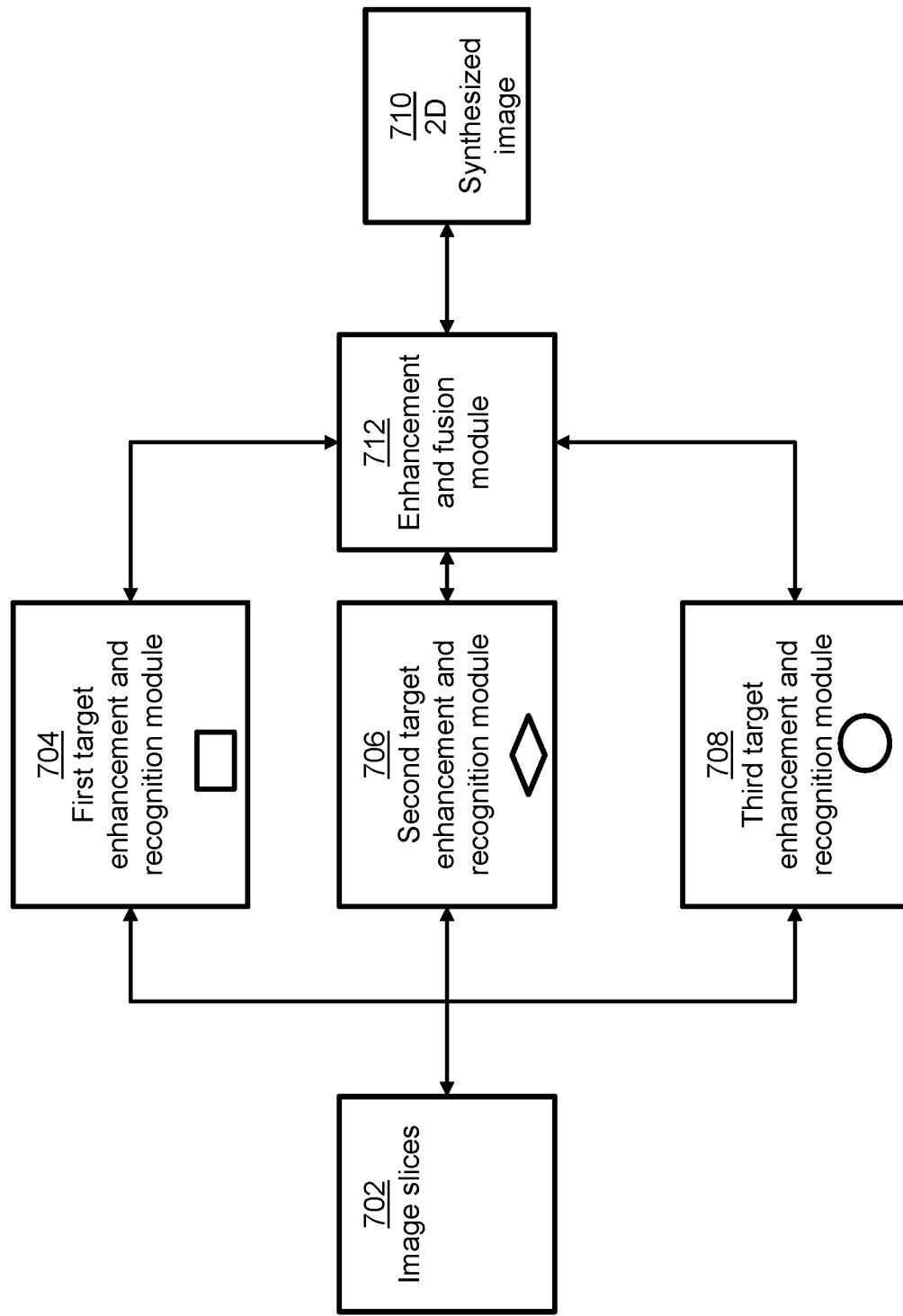
FIGS. 7A and 7B illustrate a parallel combination technique of combining data from multiple target object synthesis modules.

Another approach to running multiple target object synthesis modules on a set of image slices is illustrated in FIG. 7A. As can be seen, rather than running the multiple target object recognition/enhancement modules sequentially with the last-run target object synthesis module having the highest priority, all the target object recognition/enhancement modules may be applied in parallel. In particular, one or more enhancement or fusion modules 712 may be utilized to ensure that the various objects are combined appropriately on the 2D synthesized image. This approach may not follow a hierarchical approach, and all of the objects may be given equal weight.

The image slices 702 are fed through three different target object recognition/enhancement modules, 704, 706 and 708, in parallel. The first target object recognition/enhancement module 604 (associated with square-shaped object), the second target object recognition/enhancement module 606 (associated with diamond-shaped object), and the third target object recognition/enhancement module 608 (associated with circular-shaped object) are all run in parallel on the image slices 702. In some embodiments, an enhancement and fusion module 712 may be utilized to ensure that the different objects are fused together appropriately in case of overlap between multiple objects. The target object recognition/enhancement modules 704, 706 and 708, run in parallel may generate the 2D synthesized image 710.

Figure 7B:
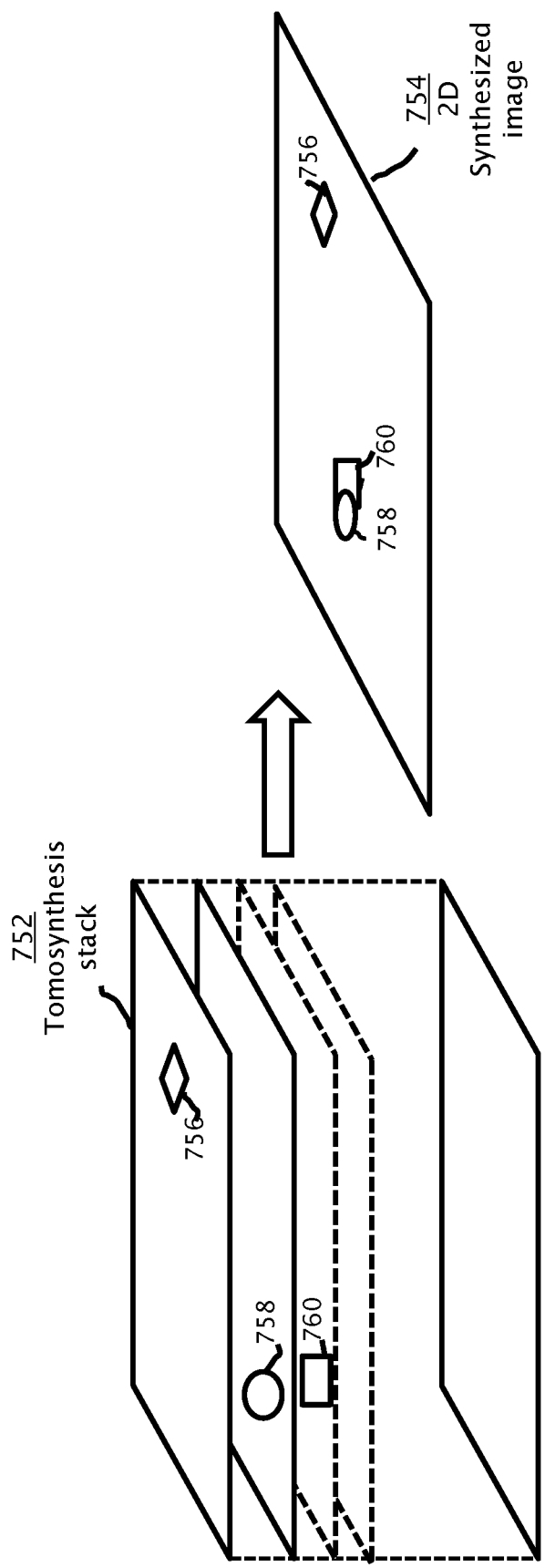

This approach to combining various object types in parallel is illustrated in FIG. 7B. In particular, the tomosynthesis stack 752 depict the same objects as FIG. 6B (e.g., objects 756, 758 and 760) at various image slices. As illustrated, objects 758 and 760 somewhat overlap in the z direction, which means that they are likely to compete for representation and/or overlap in the 2D synthesized image 754. Here, because the multiple target object recognition/enhancement modules are run in parallel, rather than one object type overriding another object type, as was the case in FIG. 6B, both the square-object 760 and the circular object 758 are fused together in the 2D synthesized image 754. Thus, this approach does not assume an innate priority/hierarchy between objects and all objects may be fused together appropriately in the 2D synthesized image 754.

Figure 8A:
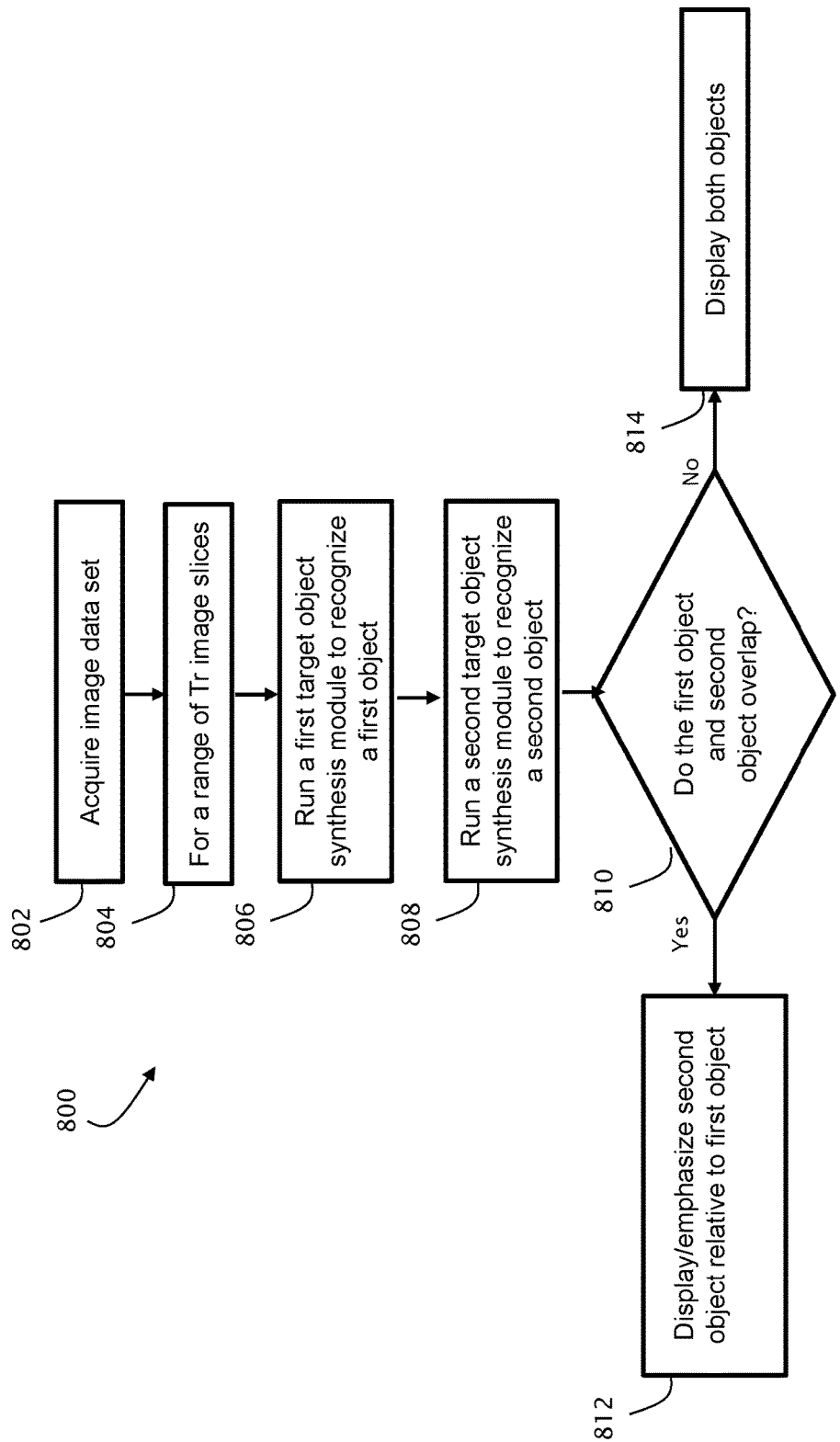
FIGS. 8A and 8B illustrate two example flow diagrams of generating 2D synthesized images using the sequential combination and parallel combination techniques respectively.

FIG. 8A depicts a flow diagram 800 that illustrates exemplary steps that may be performed in an image merge process carried out in accordance with the sequential combination approach outlined above in conjunction with FIGS. 6A and 6B. At step 802, an image data set is acquired. The image data set may be acquired by a tomosynthesis acquisition system, a combination tomosynthesis/mammography system, or by retrieving pre-existing image data from a storage device, whether locally or remotely located relative to an image display device. At steps 804 and 806, for a range of 2D images (e.g., Tr stack), a first target object recognition/enhancement module is run in order to recognize a first object associated with the first target object recognition/enhancement module. Any recognized objects may be stored in a storage module associated with the first target object recognition/enhancement module. At step 808, a second target object recognition/enhancement module is run in order to recognize a second object associated with the second target object recognition/enhancement module. At step 810, it may be determined whether the first recognize object and the second recognized object overlap each other in the z direction. If it is determined that the two objects overlap, only the second object may be displayed (or otherwise emphasized over the first object) on the 2D synthesized image at step 812. If, on the other hand, it is determined that the two objects do not overlap, both objects are displayed on the 2D synthesized image at step 814.

Figure 8B:
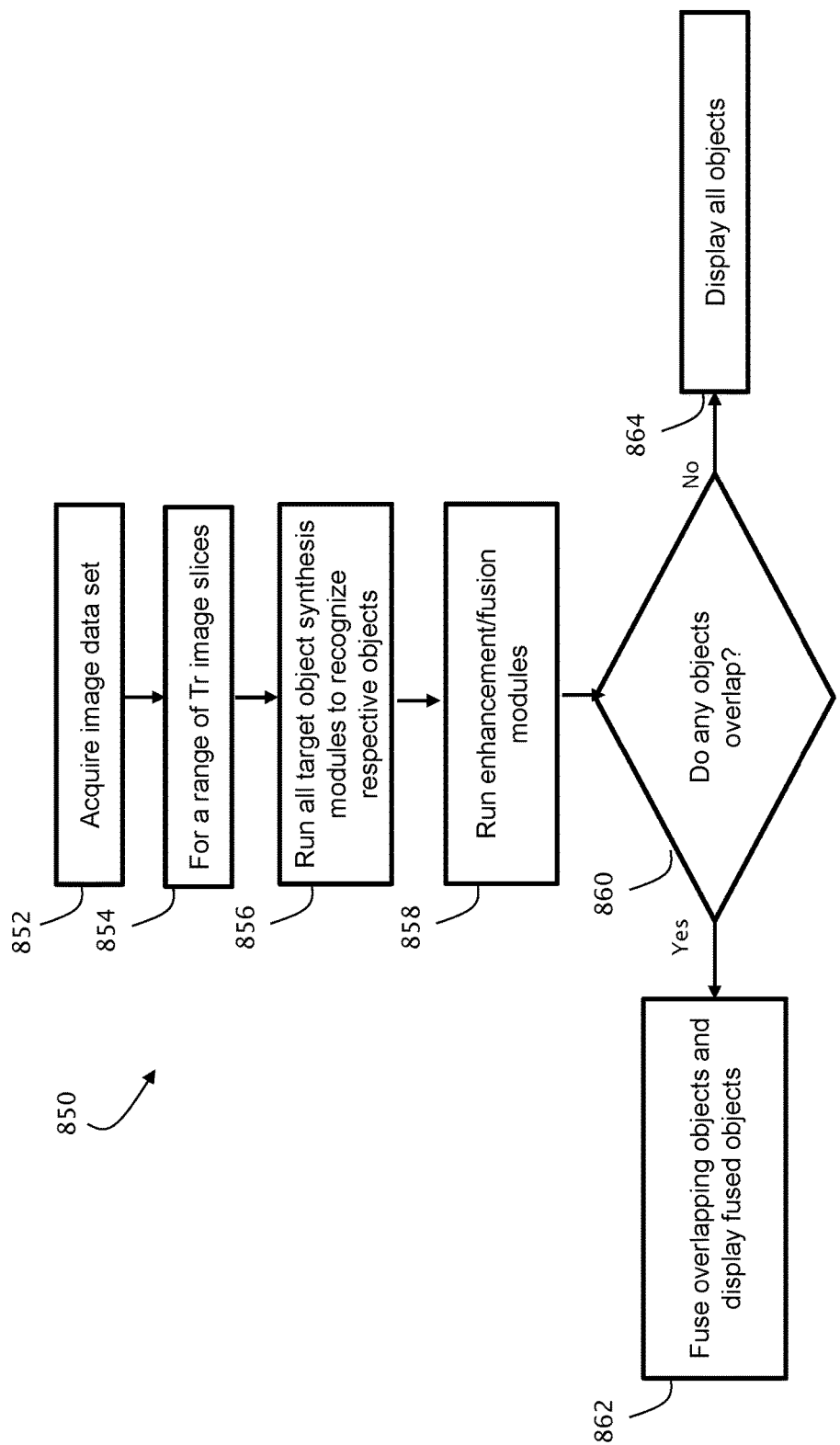

FIG. 8B depicts a flow diagram 850 that illustrates exemplary steps that may be performed in an image synthesis process carried out in accordance with the parallel combination approach outlined above in conjunction with FIGS. 7A and 7B. At step 852, an image data set is acquired. The image data set may be acquired by a tomosynthesis acquisition system, a combination tomosynthesis/mammography system, or by retrieving pre-existing image data from a storage device, whether locally or remotely located relative to an image display device. At steps 854 and 856, for a range of 2D images (e.g., Tr stack), all the programmed target object recognition/enhancement modules are run to recognize respective objects in the Tr image stack. At step 858, one or more enhancement modules may also be run to determine whether a fusion process needs to occur. At step 860, it may be determined whether any recognized objects overlap in the z direction. If it is determined that any two (or more) objects overlap, the overlapping objects may be fused together, at step 862. If, on the other hand, it is determined that no objects overlap, all the objects are displayed as is on the 2D synthesized image at step 814.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. It will also be apparent to those skilled in the art that various changes and modifications may be made to the depicted and/or described embodiments (e.g., the dimensions of various parts), without departing from the scope of the disclosed inventions, which is to be defined only by the following claims and their equivalents. The specification and drawings are, accordingly, to be regarded in an illustrative rather than restrictive sense.

What is claimed is:

1. A method for processing breast tissue image data, comprising:
    processing image data of a patient's breast tissue to generate a set of image slices that collectively depict the patient's breast tissue, wherein at least two image slices in the set of image slices comprise at least a first object of a first object type and a second object of a second object type;
    recognizing, based on a first object recognition process, the first object of the first type;
    assigning, based on one or more characteristics of the first object recognition process, a first weight to the first object;
    recognizing, based on a second object recognition process, the second object of the second type;
    assigning, based on one or more characteristics of the first and second object recognition process, a second weight to the second object, wherein the second weight is greater than the first weight;
    populating the first object and the second object to a high-dimensional grid;
    determining, based on populating the first object and the second object to a high-dimensional grid, that the first object and the second object overlap;
    generating a synthesized image of the patient's breast tissue wherein the second object is emphasized relative to the first object; and
    displaying the synthesized image.

2. The method of claim 1, wherein the first object recognition process and the second object recognition process are performed sequentially.

3. The method of claim 2, wherein the second object recognition process is performed after the first object recognition process.

4. The method of claim 1, wherein the first object recognition process and the second object recognition process are performed in parallel.

5. The method of claim 1, wherein the second object is determined to be more clinically significant based on the one or more characteristics of the first and second object recognition process.

6. The method of claim 1, wherein the first object is fully obscured by the second object.

7. The method of claim 1, wherein generating a synthesized image of the patient's breast tissue wherein the second object is emphasized relative to the first object comprises increasing a transparency associated with the first object.

8. The method of claim 1, wherein the first object and the second object are determined to both be part of one high-dimensional object.

9. The method of claim 8, wherein the second object is a central portion of the high-dimensional object and the first object is a peripheral portion of the high-dimensional object.

10. The method of claim 1, further comprising determining, based on the first and second object recognition process and populating the first and second object to the high-dimensional grid, that the first and second object are two discrete objects.

11. The method of claim 1, wherein recognizing, based on the first object recognition process, and recognizing, based on the second object recognition process, comprises communication, by the first and second object recognition processes, with a storage of recognized objects.

12. The method of claim 1, wherein recognizing, by the first object recognition process, comprises communication, by a first object recognition module, with a storage of recognized first objects and recognizing, by the second object recognition process, comprises communication, by the second object recognition module, with a storage of recognized second objects.

13. The method of claim 12, wherein the storage of recognized first objects and the storage of recognized second objects are two discrete storages.

14. The method of claim 12, further comprising updating, by the first object recognition process, the storage of recognized first objects based on one or more recognized first objects; and updating, by the second object recognition process, the storage of recognized second objects based on one or more recognized second objects.

\* \* \* \* \*